(12) United States Patent
Shiho et al.

(10) Patent No.: US 6,875,518 B2
(45) Date of Patent: Apr. 5, 2005

(54) RUTHENIUM FILM, RUTHENIUM OXIDE FILM AND PROCESS FOR FORMING THE SAME

(75) Inventors: Hiroshi Shiho, Tokyo (JP); Hitoshi Kato, Tokyo (JP); Yasuo Matsuki, Tokyo (JP); Satoshi Ebata, Tokyo (JP); Yoichiro Maruyama, Tokyo (JP); Yasuaki Yokoyama, Tokyo (JP)

(73) Assignee: JSR Corporation, Tokyo (JP)

( * ) Notice: Subject to any disclaimer, the term of this patent is extended or adjusted under 35 U.S.C. 154(b) by 230 days.

(21) Appl. No.: 10/168,104

(22) PCT Filed: Oct. 16, 2001

(86) PCT No.: PCT/JP01/09067

§ 371 (c)(1),
(2), (4) Date: Jun. 17, 2002

(87) PCT Pub. No.: WO02/32839

PCT Pub. Date: Apr. 25, 2002

(65) Prior Publication Data

US 2003/0008157 A1 Jan. 9, 2003

(30) Foreign Application Priority Data

Oct. 18, 2000 (JP) .................................. 2000-318375
Oct. 26, 2000 (JP) .................................. 2000-327613
Dec. 11, 2000 (JP) .................................. 2000-375771

(51) Int. Cl.[7] .......................... B32B 15/04; B32B 9/00; C07F 15/00; C07F 17/02; C23C 16/00
(52) U.S. Cl. ................... 428/457; 428/702; 556/136; 556/137; 427/255.28; 427/255.31; 427/376.2
(58) Field of Search ........................ 428/689, 702, 428/457; 427/255.28, 255.31, 255.395, 376.2, 126.5; 556/136, 137

(56) References Cited

U.S. PATENT DOCUMENTS 4,250,210 A  2/1981  Crosby et al.
5,559,262 A * 9/1996  Beatty et al. ............... 556/20
5,874,364 A  2/1999  Nakabayashi et al.
6,303,809 B1 * 10/2001  Chi et al. .................. 556/136
6,316,064 B1 * 11/2001  Onozawa et al. ........... 427/585

FOREIGN PATENT DOCUMENTS

| JP | 6-283438 | | 10/1994 |
| JP | 049081 | * | 2/1997 |
| JP | 9-49081 | | 2/1997 |
| JP | 11-269656 | | 10/1999 |
| JP | 212744 | * | 2/2000 |
| JP | 2000-212744 | | 8/2000 |

OTHER PUBLICATIONS

Y. Baba, et al., Summary of Lectures at the Convention of Surface Technology Association, pps. 164–165, "Chemical Deposition of $RUO_2$ Thin Film from Aqueous Solution of Ruthenium Complex," Feb. 17, 1990 ( with partial English translation).

(Continued)

Primary Examiner—Brian K. Talbot
(74) Attorney, Agent, or Firm—Oblon, Spivak, McClelland, Maier & Neustadt, P.C.

(57) ABSTRACT

A composition capable of forming a metal ruthenium film and a ruthenium oxide film by a simple application/baking process, a process for forming a metal ruthenium film and a ruthenium oxide film from the composition, a metal ruthenium film and a ruthenium oxide film formed by the process, and electrodes formed of the films.

A solution composition comprising a specific ruthenium complex. The coating film of this solution composition is heated in an atmosphere containing no oxygen or an atmosphere containing oxygen to form a metal ruthenium film or a ruthenium oxide film, respectively, and electrodes formed of the films.

16 Claims, 11 Drawing Sheets

OTHER PUBLICATIONS

T. Aoyama, et al., Jpn. J. Appl. Phys., vol. 38, Part 2 No. 10A, pps. 1134–1136, "Ruthenium Films Prepared by Liquid Source Chemical Vapor Deposition Using Bis–(Ethylcyclopentadienyl)Ruthenium," Oct. 1, 1999.

P. Legzdins, et al., J. Chem. Soc. A, pps. 3322–3326, "The Protonation of Ruthenium– and Rhodium–Bridged Carboxylates and Their Use as Homogeneous Hydrogenation Catalysts For Unsaturated Substances †," 1970.

A, Spencer, et al., J.C.S. Dalton, pps. 1570–1577, "$\mu_3$–Oxo–Triruthenium Carboxylate Complexes †," Feb. 2, 1972.

* cited by examiner

RUTHENIUM FILM, RUTHENIUM OXIDE FILM AND PROCESS FOR FORMING THE SAME

FIELD OF THE INVENTION

The present invention relates to a composition suitable for forming a metal ruthenium thin film and a ruthenium oxide thin film, a process for forming a metal ruthenium thin film and a ruthenium oxide thin film from the composition, a ruthenium film and a ruthenium oxide film formed by the process, and electrodes composed of the films.

DESCRIPTION OF THE PRIOR ART

In DRAM (Dynamic Random Access Memory), a laminate film (ON film) comprising silicon oxide and silicon nitride has been used as a dielectric for insulating a capacitor and capacity has been ensured by a 3-D memory cell structure. However, along with a recent tendency to rapidly improve the integration and reduce the pattern width of DRAM, it is becoming difficult to ensure the capacity of a memory cell with prior art methods.

Then, studies on materials having a perofskite type crystal structure and a much higher dielectric constant than the ON film, such as barium titanate, strontium titanate and PZT, are now under way to further reduce the pattern width. However, even when such a super high dielectric material is used in an insulating film for capacitors, a low dielectric layer may be formed at the interface between an electrode and a dielectric, which prevents an increase in the capacity of a capacitor. It is considered that this low dielectric layer is formed by the movement of oxygen atoms from the dielectric layer to the electrode material. Therefore, use of platinum, or ruthenium as an electrode material which hardly takes in oxygen from the dielectric layer, or ruthenium oxide as an electrode material which an oxide has conductivity as it is, is now under study. Out of these, a platinum film is difficult to be dry etched whereas a metal ruthenium film or a ruthenium oxide film can be relatively easily dry etched and can be therefore advantageously used as an electrode for a capacitor comprising a perofskite type structure dielectric in the insulating film.

Sputtering is widely used to form the above metal ruthenium film and reactive sputtering is widely used to form the above ruthenium oxide film. Studies on a CVD process are also under way to obtain a finer structure and enable mass-production.

All of the above processes not only require bulky apparatuses which are expensive but also consume a large amount of energy for a vacuum system and a plasma system, thereby boosting the product cost.

A process for applying a liquid ruthenium compound without using a vacuum system has recently been proposed. "Hyomen Gijutsu Kyokai Koen Taikei Koen Yohshishuu (Summary of Lectures at the Convention of the Surface Technology Association)" (1990) discloses on page 164 a process for obtaining metal ruthenium by applying an aqueous solution of $Ru(NH_3)_6Cl_2$ and baking it. In this process, the formed metal ruthenium is in the form of fine particles and not a uniform film. "Jpn. J. Appl. Phys. 38, p. 1134 (1999)" discloses a process for forming a metal ruthenium film from liquid $Ru(EtCp)_2$ by CVD in order to increase steam pressure. In this process, a large amount of carbon remains in the ruthenium film as an impurity. Therefore, the formed metal ruthenium film is not suitable for use as a material for capacitor electrodes.

SUMMARY OF THE INVENTION

It is an object of the present invention to provide a composition capable of forming a metal ruthenium film and a ruthenium oxide film by a simple application/baking process, a process for forming a metal ruthenium film and a ruthenium oxide film from the composition, a metal ruthenium film and a ruthenium oxide film formed by the process, and electrodes composed of the films.

Other objects and advantages of the present invention will become apparent from the following description.

According to the present invention, firstly, the above objects and advantages of the present invention are attained by a solution composition for forming a film, which comprises at least one ruthenium complex selected from the group consisting of a complex of ruthenium and a β-diketone, a complex of ruthenium and a β-ketocarboxylic acid ester, a complex of ruthenium and a β-dicarboxylic acid ester, a ruthenium complex represented by the following formula (1):

wherein COT' is a ligand represented by the following formula (2):

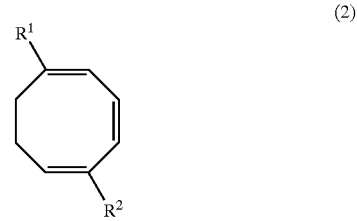

wherein $R^1$ and $R^2$ are each independently a hydrogen atom or alkyl group having 1 to 5 carbon atoms,
and COD' is a ligand represented by the following formula (3):

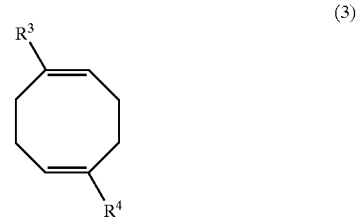

wherein $R^3$ and $R^4$ are each independently a hydrogen atom or alkyl group having 1 to 5 carbon atoms,
and a ruthenium complex having an acyloxy group represented by the following formula (4):

wherein $R^5$ is a hydrogen atom, alkyl group having 1 to 18 carbon atoms or alkenyl group having 2 to 18 carbon atoms, or a biscarboxylato group represented by the following formula (5):

According to the present invention, secondly, the above objects and advantages of the present invention are attained by a film comprising at least one ruthenium complex selected from the group consisting of a complex of ruthenium and a β-diketone, a complex of ruthenium and a β-ketocarboxylic acid ester, a complex of ruthenium and a β-dicarboxylic acid ester, a ruthenium complex represented by the following formula (1):

wherein COT' is a ligand represented by the following formula (2):

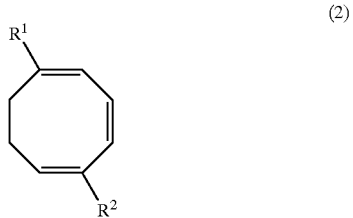

wherein $R^1$ and $R^2$ are each independently a hydrogen atom or alkyl group having 1 to 5 carbon atoms,
and COD' is a ligand represented by the following formula (3):

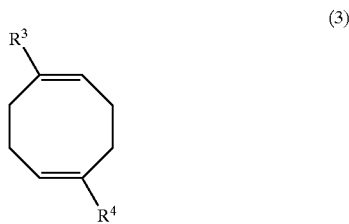

wherein $R^3$ and $R^4$ are each independently a hydrogen atom or alkyl group having 1 to 5 carbon atoms,
and a ruthenium complex having an acyloxy group represented by the following formula (4):

wherein $R^5$ is a hydrogen atom, alkyl group having 1 to 18 carbon atoms or alkenyl group having 2 to 18 carbon atoms, or a biscarboxylato group represented by the following formula (5):

According to the present invention, thirdly, the above objects and advantages of the present invention are attained by a process for forming a ruthenium film, comprising applying the solution composition of the present invention to a substrate and heating it in an atmosphere containing substantially no oxygen (may be referred to as "first process of the present invention" hereinafter).

According to the present invention, in the fourth place, the above objects and advantages of the present invention are attained by a process for forming a ruthenium oxide film, comprising applying the solution composition of the present invention to a substrate and heating it in an atmosphere containing oxygen (may be referred to as "second process of the present invention" hereinafter).

According to the present invention, in the fifth place, the above objects and advantages of the present invention are attained by a ruthenium film formed by the first process of the present invention.

According to the present invention, in the sixth place, the above objects and advantages of the present invention are attained by a ruthenium oxide film formed by the second process of the present invention.

According to the present invention, in the seventh place, the above objects and advantages of the present invention are attained by a process for producing a ruthenium electrode in the same manner as the first process of the present invention.

According to the present invention, in the eighth place, the above objects and advantages of the present invention are attained by a process for producing a ruthenium oxide electrode in the same manner as the second process of the present invention.

According to the present invention, finally, the above objects and advantages of the present invention are attained by electrodes formed by the above processes for producing an electrode.

DETAILED DESCRIPTION OF THE PREFERRED EMBODIMENTS

Figure 1:
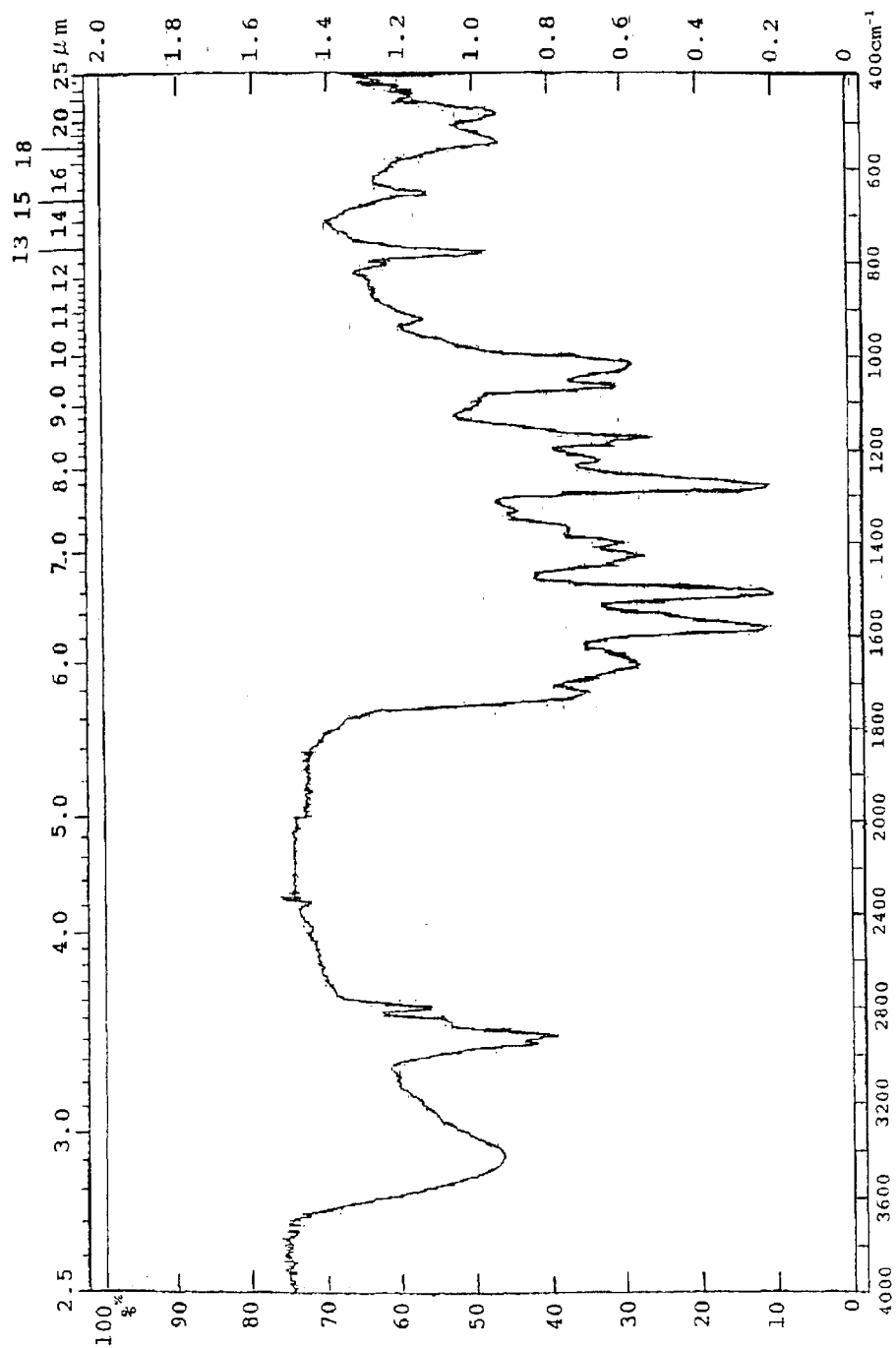
FIG. 1 is an IR spectrum diagram of a complex of ruthenium and ethyl acetoacetate obtained in Synthetic Example 1.

The ruthenium complex used in the present invention is selected from a complex of ruthenium and a β-diketone, a complex of ruthenium and a β-ketocarboxylic acid ester, a complex of ruthenium and a β-dicarboxylic acid ester, a ruthenium complex represented by the above formula (1) and a ruthenium complex represented by the above formula (2).

Out of these, examples of the complex of ruthenium and a β-diketone, complex of ruthenium and a β-ketocarboxylic acid ester and complex of ruthenium and a dicarboxylic acid ester include complexes represented by the following formulas (6) to (12).

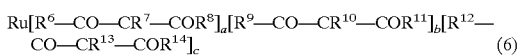

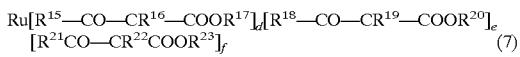

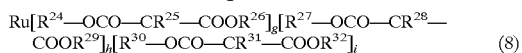

$$Ru[R^{24}\text{—OCO—}CR^{25}\text{—}COOR^{26}]_g[R^{27}\text{—OCO—}CR^{28}\text{—}COOR^{29}]_h[R^{30}\text{—OCO—}CR^{31}\text{—}COOR^{32}]_i \quad (8)$$

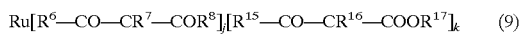

$$Ru[R^6\text{—CO—}CR^7\text{—}COR^8]_j[R^{15}\text{—CO—}CR^{16}\text{—}COOR^{17}]_k \quad (9)$$

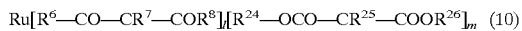

$$Ru[R^6\text{—CO—}CR^7\text{—}COR^8]_l[R^{24}\text{—OCO—}CR^{25}\text{—}COOR^{26}]_m \quad (10)$$

$$Ru[R^{15}\text{—CO—}CR^{16}\text{—}COOR^{17}]_n[R^{24}\text{—OCO—}CR^{25}\text{—}COOR^{26}]_o \quad (11)$$

$$Ru[R^{24}\text{—OCO—}CR^{25}\text{—}COOR^{26}][R^6\text{—CO—}CR^7\text{—}COR^8][R^{15}\text{—CO—}CR^{16}\text{—}COOR^{17}] \quad (12)$$

In the above formulas, a, b, c, d, e, f, g, h and i are each independently an integer of 0 to 3, j, k, l, m, n and o are each independently an integer of 1 or 2, with the proviso that a+b+c=3, d+e+f=3, g+h+i=3, j+k=3, l+m=3, and n+o=3. $R^6$, $R^8$, $R^9$, $R^{11}$, $R^{12}$, $R^{14}$, $R^{15}$, $R^{17}$, $R^{18}$, $R^{20}$, $R^{21}$, $R^{23}$, $R^{24}$, $R^{26}$, $R^{27}$, $R^{29}$, $R^{30}$ and $R^{32}$ are each independently an alkyl group having 1 to 18 carbon atoms, alkenyl group having 2 to 18 carbon atoms or aryl group, and the alkyl group or alkenyl group may have a substituent such as a halogen group or alkoxy group. $R^7$, $R^{10}$, $R^{13}$, $R^{16}$, $R^{19}$, $R^{22}$, $R^{25}$, $R^{28}$ and $R^{31}$ are each independently an alkyl group having 1 to 18 carbon atoms, alkenyl group having 2 to 18 carbon atoms, alkoxycarbonyl group having an alkyl group with 1 to 18 carbon atoms or alkenyl group, or aryl group having an alkyl group with 1 to 18 carbon atoms or alkenyl group as a substituent, and the alkyl group, the alkyl group in the alkenyl group and alkoxy group, or the alkenyl group may have a substituent such as a halogen group or alkoxy group.

Examples of the alkyl group having 1 to 18 carbon atoms include methyl group, ethyl group, propyl group, butyl group, pentyl group, hexyl group, heptyl group, octyl group, nonyl group, decyl group, undecyl group, dodecyl group, tridecyl group, tetradecyl group, hexadecyl group and octadecyl group.

Examples of the alkenyl group having 2 to 18 carbon atoms include 9-octadecenyl group, 9,12-octadecadienyl group and 9,11,13-octadecatrienyl group.

Examples of the alkoxycarbonyl group include alkoxycarbonyl groups having the above alkyl group or alkenyl group.

Examples of the aryl group include phenyl group and methylphenyl group.

The complex represented by the above formula (6) is a complex of ruthenium and a β-diketone, the complex represented by the above formula (7) is a complex of ruthenium and a β-ketocarboxylic acid ester, and the complex represented by the above formula (8) is a complex of ruthenium and a β-dicarboxylic acid ester. The complex represented by the above formula (9) has a β-diketone and a β-ketocarboxylic acid ester as ligands, the compound represented by the above formula (10) has a β-diketone and a β-dicarboxylic acid ester as ligands, and the complex represented by the above formula (12) has a β-diketone, a β-ketocarboxylic acid ester and a β-dicarboxylic acid ester as ligands. Paying attention to the fact that all of them have a β-diketone ligand, these complexes are classified into a group of complexes of ruthenium and a β-diketone in the present invention for convenience's sake.

The complex represented by the above formula (11) has a β-ketocarboxylic acid ester and a β-dicarboxylic acid ester as ligands. In the present invention, this complex is classified into a group of complexes of ruthenium and a β-ketocarboxylic acid ester for convenience's sake.

Illustrative examples of the ruthenium complexes represented by the above formulas (6) to (12) include Ru(acetylacetone)$_3$, Ru(propionylacetone)$_3$, Ru(methyl diacetylmethane)$_3$, Ru(dipropionylmethane)$_3$, Ru(n-butyrylacetone)$_3$, Ru(isobutyrylacetone)$_3$, Ru(3-methyl-2,4-hexanedione)$_3$, Ru(diacetylethylmethane)$_3$, Ru(n-valerylacctone)$_3$, Ru(propianyl-n-butyrylmethane)$_3$, Ru(3-methyl-2,4-heptanedione)$_3$, Ru(isovalerylacetone)$_3$, Ru(pivaloylacetone)$_3$, Ru(isopropyl diacetylmethane)$_3$, Ru(caproylacetone)$_3$, Ru(di-n-butyrylmethane)$_3$, Ru(2,2,6,6-tetramethyl-3,5-heptanedione)$_3$, Ru(benzoylacetone)$_3$, Ru(3-phenyl-2,4-pentanedione)$_3$, Ru(dibenzoylmethane)$_3$, Ru(ethoxycarbonyl diacetylmethane)$_3$, Ru(1,1,1,5,5,5-hexafluoro-2,4-pentanedione)$_3$, Ru(methyl acetoacetate)$_3$, Ru(ethyl acetoacetate)$_3$, Ru(methyl α-propionylpropionate)$_3$, Ru(ethyl propionylacetate)$_3$, Ru(ethyl α-methylacetoacetate)$_3$, Ru(acetylacetone)(ethyl acetoacetate)$_2$, Ru(acetylacetone)$_2$(ethyl acetoacetate), Ru(2,2,6,6-tetramethyl-3,5-heptanedione)(ethyl acetoacetate)$_2$, Ru(2,2,6,6-tetramethyl-3,5-heptanedione)$_2$ (ethyl acetoacetate), Ru(acetylacetone)(ethyl propionylacetate)$_2$, Ru(acetylacetone)$_2$(ethyl propionylacetate), Ru(acetylacetone)(ethoxycarbonyl diacetylmethane)$_2$, Ru(acetylacetone)$_2$(ethoxycarbonyl diacetylmethane), Ru(dimethyl malonate)$_3$, Ru(diethyl malonate)$_3$, Ru(dipropyl malonate)$_3$, Ru(dibutyl malonate)$_3$, Ru(dihexyl malonate)$_3$, Ru(dioctyl malonate)$_3$, Ru(diundecyl malonate)$_3$, Ru(dihexadecyl malonate)$_3$, Ru(di-9-octadecenyl malonate)$_3$, Ru(di-9,12-octadecadienyl malonate)$_3$, Ru(di-9,11,13-octadecatrienyl malonate)$_3$, Ru(diethyl malonate)(acetylacetone)(ethyl acetoacetate) and Ru(dimethyl malonate)(acetylacetone)(ethyl acetoacetate). They may be used alone or in combination of two or more.

The complex of ruthenium and a β-diketone, complex of ruthenium and a β-ketocarboxylic acid ester and complex of ruthenium and a β-dicarboxylic acid ester are produced from a carbanion synthesized from a ruthenium halide, β-diketone and β-ketocarboxylic acid ester or β-dicarboxylic acid ester, respectively.

Examples of the ruthenium halide include ruthenium trichloride, ruthenium tribromide and hydrates thereof.

The carbanion can be produced through a reaction between a metal alkoxide or metal hydride and at least one compound selected from the group consisting of a β-diketone, β-ketocarboxylic acid ester and β-dicarboxylic acid ester.

Examples of the metal alkoxide or metal hydride include sodium methoxide, sodium ethoxide, sodium t-butoxide and sodium hydride.

The above process for producing a ruthenium complex in the present invention is carried out in the presence of a solvent.

Examples of the solvent include alcohols such as methanol, ethanol, propanol, butanol, pentanol, hexanol, octanol, decanol, undecanol, dodecanol, hexadecanol, octadecanol, ethylene glycol, ethylene glycol monomethyl ether, ethylene glycol monoethyl ether, diethylene glycol monomethyl ether, diethylene glycol monoethyl ether, propylene glycol, propylene glycol monomethyl ether, propylene glycol monoethyl ether, propylene glycol monopropyl ether, glycerol, glycerol monomethyl ether, glycerol dimethyl ether, glycerol monoethyl ether and glycerol diethyl ether; cyclic ethers such as tetrahydrofuran and dioxane; aliphatic ethers such as ethylene glycol dimethyl ether, ethylene glycol diethyl ether, diethylene glycol dimethyl ether, diethylene glycol diethyl ether, propylene glycol dimethyl ether, propylene glycol diethyl ether, glycerol trimethyl ether and glycerol triethyl ether; esters having an ether group such as ethylene glycol monomethyl ether acetate and ethylene glycol monoethyl ether acetate; and esters having a hydroxyl group such as methyl lactate and ethyl lactate.

The ruthenium complex used as a raw material in the present invention includes a ruthenium complex represented by the above formula (1). In the formula (1), COT' is represented by the above formula (2) and COD' is represented by the above formula (3).

R[1] and R[2] in the formula (2) are each independently a hydrogen atom or alkyl group having 1 to 5 carbon atoms and R[3] and R[4] in the formula (3) are defined the same.

Examples of the ligand (COT') represented by the formula (2) include 1,3,5-cyclooctatriene (may be abbreviated as COT hereinafter), 1,5-dimethyl-1,3,5-cyclooctatriene and 1,5-diethyl-1,3,5-cyclooctatriene.

Examples of the ligand (COD') represented by the formula (3) include 1,5-cyclooctadiene (may be abbreviated as COD hereinafter), 1,5-dimethyl-1,5-cyclooctadiene and 1,5-diethyl-1,5-cyclooctadiene.

The ruthenium complex represented by the above formula (1) is a complex compound having a ligand represented by the above formula (2) and a ligand represented by the above formula (3) coordinately bonded to a ruthenium atom.

The ruthenium complex used as a raw material in the present invention includes a ruthenium complex having a group represented by the above formula (4) or (5).

The ruthenium complex having a group represented by the above formula (4) is a complex compound having a RCOO group and, in certain cases, an oxygen atom and/or $H_2O$ molecule coordinately bonded to a ruthenium atom.

The above ruthenium complex is represented by the following formula (1'), for example:

$$(Ru)_p(O)_q(R^5COO)_r(H_2O)_s \quad (1')$$

wherein R is as defined in the above formula (1), p and r are each independently an integer of 1 to 6, and q and s are each independently an integer of 0 to 6.

The $R^5COO$ group means the residual group after a hydrogen atom bonded to oxygen is excluded from a carboxylic acid. R is preferably exemplified by hydrogen atom; alkyl groups such as methyl group, ethyl group, propyl group, butyl group, pentyl group, hexyl group, heptyl group, octyl group, nonyl group, decyl group, $CH_3(CH_2)_3CH(C_2H_5)$ group, undecyl group, dodecyl group, tridecyl group, tetradecyl group, hexadecyl group and octadecyl group; and alkenyl groups such as 9-octadecenyl group, 9,12-octadecadienyl group and 9,11,13-octadecatrienyl group. These alkyl groups and alkenyl groups may be linear, cyclic or branched.

Out of these, hydrogen atom, methyl group and $CH_3(CH_2)_3CH(C_2H_5)$ group are preferred.

p and r are each an integer of 1 to 6, and q and s are each an integer of 0 to 6. p, q, r and s are determined by the type of $R^5$ in the compound represented by the formula (1'). For example, when $R^5$ is a methyl group or $CH_3(CH_2)_3CH(C_2H_5)$ group, p=3, q=1, r=6 and s=3.

The ruthenium complex represented by the formula (2) is a complex compound having a $(COO)_2$ group and, in certain cases, an oxygen atom and/or $H_2O$ molecule coordinately bonded to a ruthenium atom.

The above ruthenium complex is represented by the following formula (2'), for example:

$$(Ru)_p(O)_q[(COO)_2]_t(H_2O)_s \quad (2')$$

p and t are each an integer of 1 to 6, q and s are each an integer of 0 to 6. p, q, s and t are determined by synthesis conditions. For example, p=3, q=1, s=3 and t=3.

The above ruthenium complex can be synthesized by methods disclosed in J. Chem. Soc. (A), p. 3322–3326 (1970) and J. C. S. Dalton, p. 1570–1577 (1972). More specifically, it can be synthesized by reacting a ruthenium trichloride hydrate with a carboxylic acid corresponding to a $R^5COO$ group or $(COO)_2$ group or an alkali metal salt of the carboxylic acid in an alcohol solvent. The alkali metal used in the alkali metal salt of the carboxylic acid is selected from lithium, potassium and sodium. Examples of the alcohol used as a solvent include methanol, ethanol, propanol, butanol, pentanol, hexanol, octanol, decanol, undecanol, dodecanol, hexadecanol and octadecanol.

In the present invention, the above ruthenium complexes may be used alone or in combination of two or more.

The solution composition of the present invention is advantageously provided as a solution of a ruthenium complex dissolved in a solvent. The solvent used is not particularly limited if it dissolves the ruthenium complex and does not react with a solvent. Examples of the solvent include hydrocarbon-based solvents such as n-pentane, cyclopentane, n-hexane, cyclohexane, n-heptane, cycloheptane, n-octane, cyclooctane, decane, cyclodecane, dicyclopentadiene hydride, benzene, toluene, xylene, durene, indene, tetrahydronaphthalene, decahydronaphthalene and squalane; ether-based solvents such as diethyl ether, dipropyl ether, dibutyl ether, ethylene glycol dimethyl ether, ethylene glycol diethyl ether, ethylene glycol methyl ethyl ether, diethylene glycol dimethyl ether, diethylene glycol diethyl ether, diethylene glycol methyl ethyl ether, propylene glycol monomethyl ether acetate, tetrahydrofuran, tetrahydropyran, bis(2-methoxyethyl)ether and p-dioxane; polar solvents such as propylene carbonate, γ-butyrolactone, N-methyl-2-pyrrolidone, dimethyl formamide, acetonitrile, dimethyl sulfoxide, methylene chloride and chloroform; alcohol-based solvents such as methanol, ethanol, propanol, butanol, hexanol, cyclohexanol, octanol, decanol, ethylene glycol, ethylene glycol monomethyl ether, ethylene glycol monoethyl ether, diethylene glycol monomethyl ether, diethylene glycol monoethyl ether, propylene glycol, propylene glycol monomethyl ether, propylene glycol monoethyl ether, propylene glycol monopropyl ether, glycerol, glycerol monomethyl ether, glycerol dimethyl ether, glycerol monoethyl ether and glycerol diethyl ether; esters having a hydroxyl group such as methyl lactate and ethyl lactate; and water. Out of these, alcohol-based solvents and mixtures of an alcohol-based solvent and a hydrocarbon-based solvent or the above polar solvent are preferred from the viewpoints of solubility of a ruthenium complex and stability of a solution thereof. These solvents may be used alone or in combination of two or more.

The content of a ruthenium complex in the solution composition of the present invention is preferably 1 to 50 wt %. It may be suitably adjusted according to a desired thickness of a ruthenium film. To increase the content of the ruthenium atom in the solution, another ruthenium compound may be optionally used. Examples of the another ruthenium compound include compounds which have been used as a raw material for CVD, such as $Ru(cyclopentadienyl)_2$, $Ru(ethylcyclopentadienyl)_2$, $Ru_3(CO)_{12}$ and $Ru(CO)_4$(hexafluoro-2-butyne), ruthenium complexes such as Ru(cyclooctadiene)(pentadiene), Ru(bicyclo[2.2.1]heptadiene)(pentadiene), Ru(cyclohexatriene)(diethylene), Ru(hexamethylcyclohexatriene)(diethylene), Ru(cyclohexatriene)(cyclohexadiene), Ru(hexamethylcyclohexatriene)(cyclohexadiene), Ru(cyclohexatriene)(bicyclo[2.2.1]heptadiene) and Ru(hexamethylcyclohexatriene)(bicyclo[2.2.1]heptadiene), and Ru(cyclooctatriene)(cyclooctadiene) complex.

The amount of the another ruthenium compound is preferably 20 wt % or less based on 100 parts by weight of the ruthenium complex. When the amount is larger than 20 wt %, film forming properties tend to deteriorate.

A fluorine-based, silicone-based or nonionic-based surface tension modifier may be added to the solution composition of the present invention as required in a small amount that does not prevent the targeted function from being developed.

The solution composition of the present invention may be suitably mixed with fine particles of a metal oxide such as aluminum oxide, zirconium oxide, titanium oxide or silicon oxide as required. Further, a nonionic surfactant may be used to improve wettability of a material to be coated by the solution composition and the leveling of the coating film and prevent the generation of irregularities on the coating film and the formation of a citron skin-like uneven surface.

The first process and the second process of the present invention can be carried out using the solution composition of the present invention.

In all of the first process and the second process, the solution composition of the present invention is first applied to a substrate or support to form a coating film. It should be understood that the coating film as used herein includes both a coating film containing a solvent and a coating film containing no solvent. The material, shape and the like of the support are not particularly limited but the material preferably stands a heat treatment in the subsequent step and the support on which the coating film is to be formed is not limited to a particular form and may be flat or nonflat with a level difference. Examples of the material of the support include glasses, metals, plastics and ceramics. The glasses include quartz glass, borosilicated glass, soda glass and lead glass. The metals include gold, silver, copper, nickel, silicon, aluminum, iron and stainless steel. The plastics include polyimide and polyether sulfone. The shape of the material is not particularly limited and may be bulk, plate-like or film-like. The surface of the above support may be subjected to a UV treatment or chemical treatment with a coupling agent to improve its wettability by the solution composition of the present invention before use. The coating technique of the above solution may be spin coating, dip coating, curtain coating, roll coating, spray coating, ink jetting or printing. The solution composition of the present invention may be applied once or a plurality of times. To apply the coating solution of the present invention to a substrate (support) having a fine pattern, the substrate is immersed in the coating solution and irradiated with ultrasonic waves, or the coating solution is placed on the substrate and vibrated by irradiating ultrasonic waves to be applied to the substrate. The coating film may be adjusted to a suitable thickness by selecting a coating technique and the solid content of the coating solution. The thickness of the film is preferably 0.005 to 100 $\mu$m, more preferably 0.01 to 10 $\mu$m as a solid.

In the first process and the second process of the present invention, the coating film is converted into a metal ruthenium film or ruthenium oxide film by a heat treatment. The heating time is suitably selected according to film thickness and heating atmosphere but it is generally 0.5 to 500 minutes. When the heating time is shorter than 0.5 minute, the amount of the residual organic component contained in the formed ruthenium film or ruthenium oxide film may become large and when the heating time is longer than 500 minutes, the formed film may become very fragile. The solvent can be removed from the coating film by prebaking or the like before the above heat treatment.

In the first process, the heat treatment is carried out in an atmosphere containing substantially no oxygen to form a metal ruthenium film. The atmosphere is preferably an atmosphere containing hydrogen. As the hydrogen may be used a mixture of hydrogen and an inert gas such as nitrogen, helium or argon.

In the second process, the heat treatment is carried out in an atmosphere containing oxygen to form a ruthenium oxide film. The atmosphere is preferably an atmosphere of oxygen or a mixture of oxygen and nitrogen, helium or argon.

The heat treatment in the first process and the second process may be carried out under reduced pressure or increased pressure as required.

There are thus provided the metal ruthenium film and ruthenium oxide film of the present invention. The metal ruthenium film of the present invention may contain a slight amount of an impurity such as ruthenium oxide and the ruthenium oxide film may also contain a slight amount of an impurity such as metal ruthenium.

The thus obtained metal ruthenium film and ruthenium oxide film may be used as an electrode such as a capacitor electrode, solar cell electrode, condenser electrode or flat panel display electrode. The obtained metal ruthenium film and ruthenium oxide film may be subjected to an optical treatment to modify its characteristic properties. The light source used for this optical treatment is a low-pressure or high-pressure mercury lamp, deuterium lamp, discharge light of a rare gas such as argon, krypton or xenon, YAG laser, argon laser, carbonic acid gas laser, or excimer laser such as XeF, XeCl, XeBr, KrF, KrCl, ArF or ArCl. These light sources generally have an output of 10 to 5,000 W but an output of 100 to 1,000 W is enough to modify the above characteristic properties. The wavelength of the light source is not particularly limited but generally 170 to 600 nm. Laser light is particularly preferred for the modification of a ruthenium film. The temperature at the time of the optical treatment is generally room temperature. A mask may be used to illuminate only a specific portion.

Although the thickness of the ruthenium film may be suitable according to its application purpose, it is preferably 0.0005 to 10 $\mu$m (5 to 100,000 Å), more preferably 0.001 to 0.5 $\mu$m (10 to 5,000 Å).

Although the thickness of the ruthenium oxide film may be suitable likewise, it is preferably 0.001 to 100 $\mu$m (10 to 1,000,000 Å), more preferably 0.002 to 10 $\mu$m (20 to 100,000 Å).

EXAMPLES

The following examples are provided for the purpose of further illustrating the present invention but are in no way to be taken as limiting.

Synthetic Example 1

14.47 g of a 28% methanol solution of sodium methoxide was diluted with 110 ml of methanol and the obtained diluted solution was added dropwise to a solution of 9.76 g of ethyl acetoacetate dissolved in 100 ml of methanol at room temperature in about 15 minutes. After the end of addition, the resulting solution was stirred for 1 hour. The solution turned from achromatic to yellow along with agitation. A solution of 5.19 g of ruthenium trichloride dissolved in 200 ml of methanol was added dropwise to the obtained solution under agitation in about 30 minutes and then the resulting solution was heated under reflux for 5 hours and left at room temperature for 24 hours. Thereafter, the precipitated salt was removed by a membrane filter having an opening diameter of 0.45 $\mu$m, and methanol was removed by an evaporator. The residue was dissolved in 100 ml of ethanol and left at room temperature for 1 hour, the precipitated salt was removed again by a membrane filter having an opening diameter of 0.45 μm, and the filtrate was concentrated by an evaporator and dried under reduced pressure at 50° C. to obtain 9.1 g of a product. The IR spectrum of the product showed a strong absorption at 1,520 and 1,590 cm$^{-1}$ and an absorption derived from a carbonyl group at 1,720 and 1,745 cm$^{-1}$ which was seen with ethyl acetoacetate as a raw material was not seen, which proved that a complex of ruthenium and ethyl acetoacetate was obtained. The IR spectrum of the reaction product is shown in FIG. 1. The elemental analytical values of the product were as follows: Ru 20.41 (20.69), C 44.34 (44.26), H 5.65 (5.57) and O 29.60 (29.48). The figures within the parentheses are calculated values of $Ru[CH_3COCHCOOC_2H_5]_3$.

Synthetic Example 2

A complex of ruthenium, acetylacetone and ethyl acetoacetate was synthesized by carrying out a reaction under the same conditions as in Synthetic Example 1 except that a mixture of 3.76 g of acetylacetone and 4.88 g of ethyl acetoacetate was used in place of ethyl acetoacetate in Synthetic Example 1. The elemental analytical values (wt %) of this product were as follows: Ru 22.91 (22.79), C 44.84 (44.69), H 5.21 (5.46) and O 27.04 (27.06). The figures within the parentheses are calculated values of $Ru[CH_3COCHCOCH_3]_{1.5}[CH_3COCHCOOC_2H_5]_{1.5}$. The product of this Synthetic Example 2 is considered to be a complex mixture represented by $Ru[CH_3COCHCOCH_3]_x[CH_3COCHCOOC_2H_5]_y$ (wherein x and y are each an integer of 0 to 3 and x+y=3).

Synthetic Example 3

A complex of ruthenium, acetylacetone and ethyl acetoacetate was synthesized by carrying out a reaction under the same conditions as in Synthetic Example 1 except that a mixture of 2.50 g of acetylacetone and 6.51 g of ethyl acetoacetate was used in place of ethyl acetoacetate in Synthetic Example 1. The elemental analytical values (wt %) of this product were as follows: Ru 21.87 (22.05), C 45.03 (44.54), H 5.32 (5.50) and O 27.78 (27.92). The figures within the parentheses are calculated values of $Ru[CH_3COCHCOCH_3][CH_3COCHCOOC_2H_5]_2$.

Synthetic Example 4

A complex of ruthenium, acetylacetone and ethoxycarbonyl diacetylmethane was synthesized by carrying out a reaction under the same conditions as in Synthetic Example 1 except that a mixture of 5.01 g of acetylacetone and 4.30 g of ethoxycarbonyl diacetylmethane was used in place of ethyl acetoacetate in Synthetic Example 1. The elemental analytical values (wt %) of this product were as follows: Ru 21.22 (21.48), C 46.03 (45.95), H 5.47 (5.36) and O 27.28 (27.21). The figures within the parentheses are calculated values of $Ru[CH_3COCHCOCH_3]_2[CH_3COC(COOC_2H_5)COCH_3]$.

Synthetic Example 5

A complex of ruthenium and ethoxycarbonyl diacetylmethane was synthesized by carrying out a reaction under the same conditions as in Synthetic Example 1 except that 12.91 g of ethoxycarbonyl diacetylmethane was used in place of ethyl acetoacetate in Synthetic Example 1. The elemental analytical values (wt %) of this product were as follows: Ru 16.58 (16.45), C 46.23 (46.90), H 5.61 (5.41) and O 31.58 (31.24). The figures within the parentheses are calculated values of $Ru[CH_3COC(COOC_2H_5)COCH_3]_3$.

Synthetic Example 6

The inside of a 500-ml three-necked flask equipped with a thermometer, capacitor and dropping funnel was substituted by argon gas, 60 g of zinc powders, 50 ml of methanol and 1,5-cyclooctadiene were fed to the flask, and a solution of 5.3 g of ruthenium trichloride trihydrate dissolved in 120 ml of methanol was slowly added dropwise from the dropping funnel to the flask under agitation with ultrasonic waves at 70° C. After the end of addition, the resulting solution was stirred with ultrasonic waves at 70° C. for another 2 hours. After the end of the reaction, the reaction solution was let pass through a Celite column to remove an undissolved product and the eluate was concentrated under reduced pressure to obtain a dark brown oily product. A solution extracted from this with cyclohexane was purified by alumina column chromatography and then recrystallized by pentane to obtain 5.5 g of a yellow crystal. It was found from its NMR spectrum that this was Ru(COT)(COD) of interest having a melting point of 92 to 93° C.

Synthetic Example 7

6.67 g of ruthenium chloride, 8.04 g of sodium acetate hydrate, 165 ml of acetic acid and 165 ml of ethanol were weighed, placed in a 500 ml eggplant-like flask and refluxed to be reacted with one another. The color of the reaction solution turned from black to greenish black along with the proceeding of the reaction. After 4 hours of the reaction, the temperature was returned to room temperature, and the reaction solution was concentrated and dried up under reduced pressure. The concentrated solid was dissolved in a small amount of ethanol, 100 ml of acetone was added, and the resulting solution was left at 5° C. After the precipitated undissolved product was removed, the acetone solution was concentrated and dried up under reduced pressure to obtain 7.8 g of a greenish black product. The IR spectrum of the product showed a strong broad absorption derived from a COOH group at 1,420 and 1,560 cm$^{-1}$ and a strong broad absorption derived from an OH group at 3,450 cm$^{-1}$. The elemental analytical values (wt %) of this product were as follows: Ru 41.72 (41.68), C 19.75 (19.81), H 3.21 (3.33) and O 35.32 (35.19). The figures within the parentheses are calculated values of $Ru_3O(CH_3COO)_6(H_2O)_3$.

Figure 2:
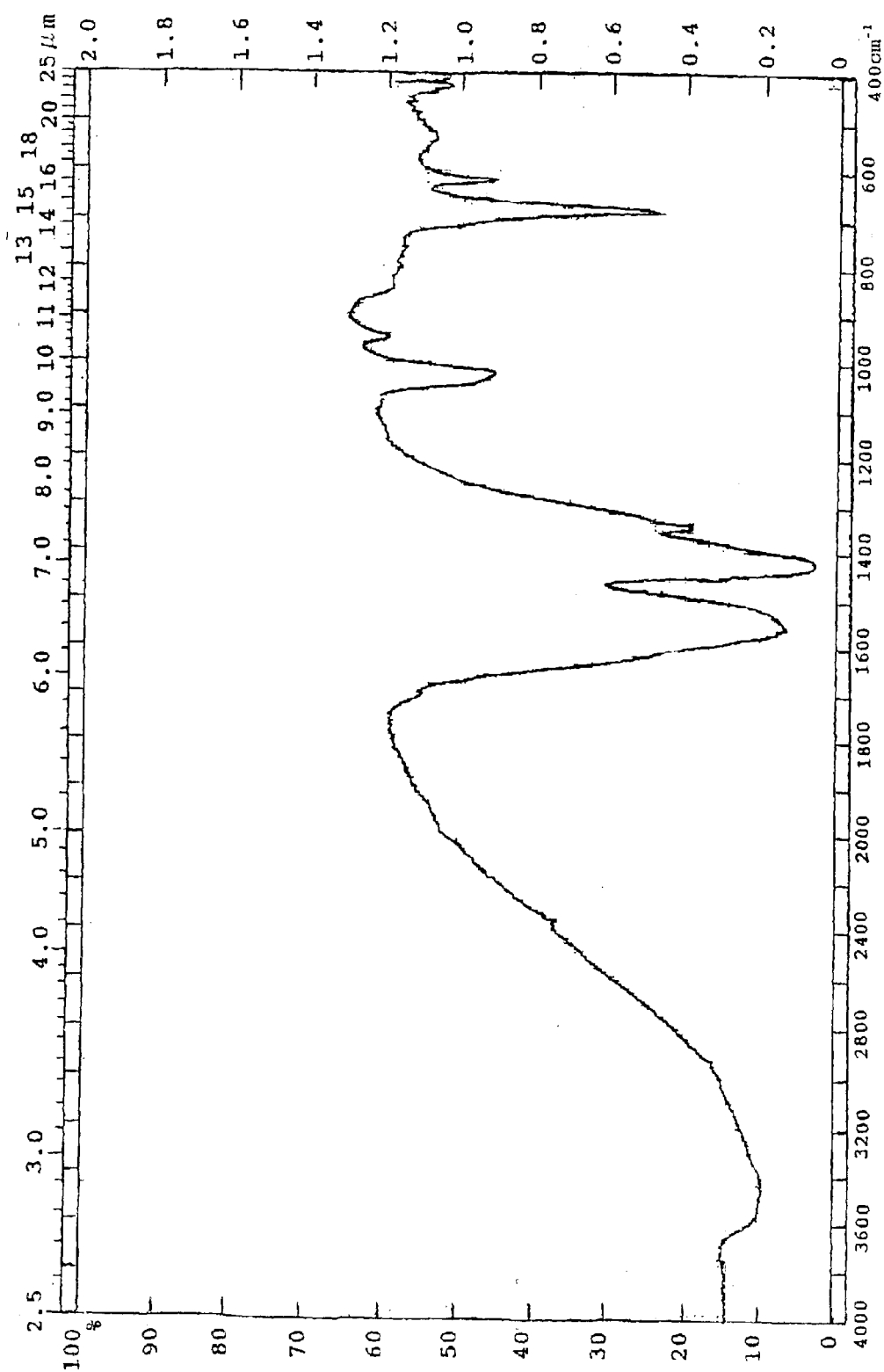
FIG. 2 is an IR spectrum diagram of a complex of ruthenium and acetic acid obtained in Synthetic Example, 7.

The IR spectrum of this product is shown in FIG. 2.

Synthetic Example 8

10.4 g of ruthenium chloride, 25.2 g of sodium bicarbonate and 300 ml of water were weighed, placed in a 500-ml eggplant-like flask and refluxed for 9 hours, and water was evaporated under reduced pressure to dry up the solution. 300 ml of acetic anhydride was further added, the resulting solution was refluxed for 3 hours to carry out a reaction, and the reaction product was obtained by purification in the same manner as in Synthetic Example 7. The IR spectrum of the product was almost the same as that of Synthetic Example 7. The elemental analytical values (wt %) of this product were as follows: Ru 41.59 (41.68), C 19.63(19.81), H 3.45 (3.33) and O 35.33 (35.19). The figures within the parentheses are calculated values of $Ru_3O(CH_3COO)_6(H_2O)_3$.

Synthetic Example 9

6.7 g of ruthenium chloride, 16.0 g of sodium 2-ethylhexanoate, 200 ml of 2-ethylhexanoic acid and 200 ml of ethanol were used to carry out a reaction in the same manner as in Synthetic Example 7. After the reaction, the reaction product was concentrated under reduced pressure, dried up and purified in the same manner as in Synthetic Example 7 to obtain a complex of ruthenium and an organic carboxylic acid (Ru-2-ethylhexanoic acid complex). The IR spectrum of the product showed a strong broad absorption derived from COO at 1,415, 1,460 and 1,510 cm$^{-1}$ and an absorption derived from CH at 2,875, 2,940 and 2,965 cm$^{-1}$. The elemental analytical values (wt %) of this product were as follows: Ru 24.41 (24.60), C 46.26 (46.78), H 7.89 (7.85) and O 21.45 (20.77). The figures within the parentheses are calculated values of $Ru_3O(C_7H_{15}COO)_6(H_2O)_3$.

Figure 3:
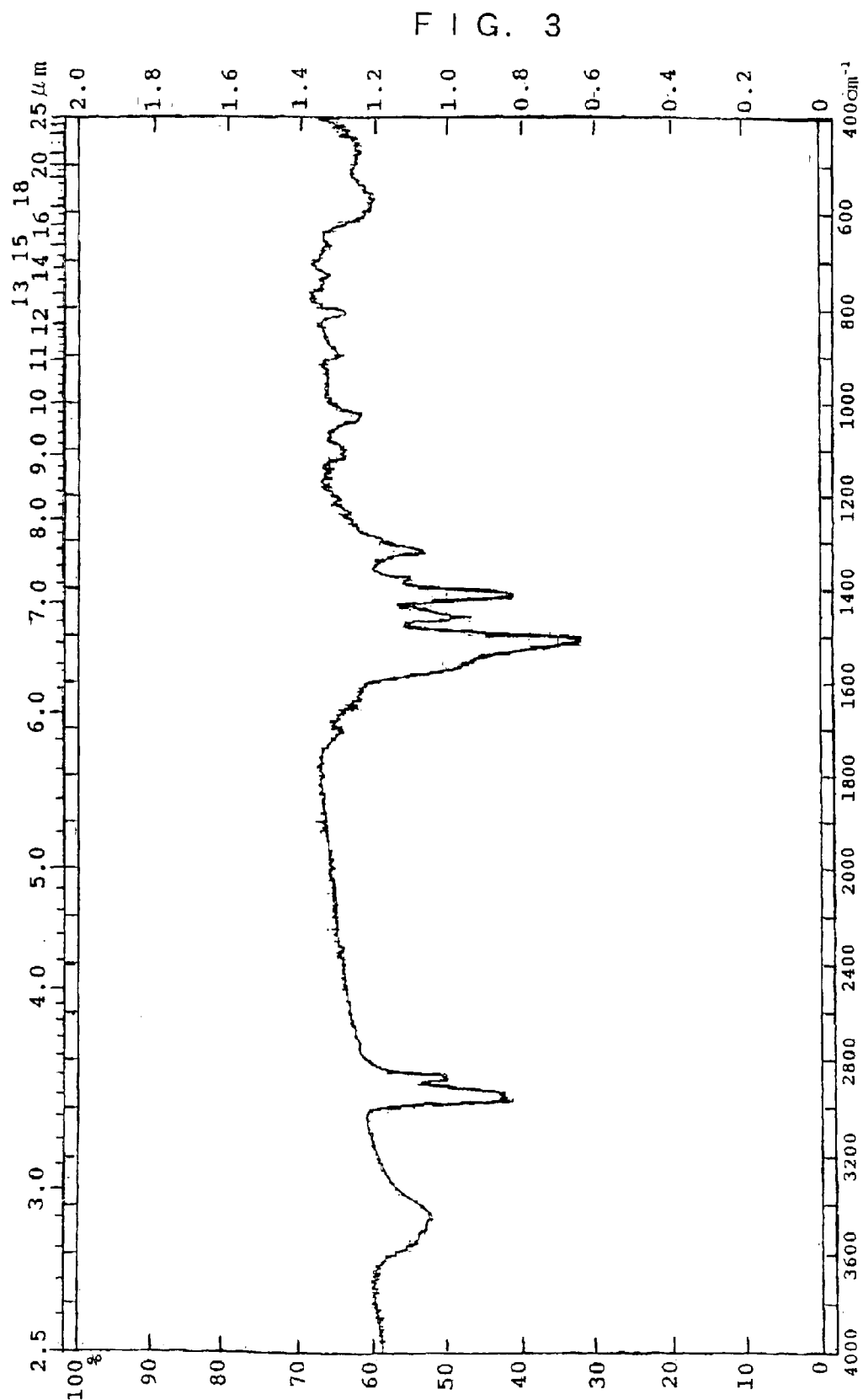
FIG. 3 is an IR spectrum diagram of a complex of ruthenium and 2-ethylhexanoic acid obtained in Synthetic Example 9.

The IR spectrum of this product is shown in FIG. 3.

Synthetic Example 10

4.2 g of ruthenium chloride, 2.7 g of sodium oxalate, 20.0 g of oxalic acid and 200 ml of ethanol were used to carry out a reaction in the same manner as in Synthetic Example 7 and the reaction product was purified to obtain a complex of ruthenium and an organic carboxylic acid (Ru-oxalic acid complex). The IR spectrum of the product showed a strong absorption derived from COO at 1,390 and 1,670 cm$^{-1}$, which proved that the product was a complex of ruthenium and an organic carboxylic acid. The elemental analytical values (wt %) of this product were as follows: Ru 47.41 (47.58), C 11.23 (11.31), H 0.90 (0.95) and O 40.46 (40.17). The figures within the parentheses are calculated values of $Ru_3O[(COO)_2]_3(H_2O)_3$.

Figure 4:
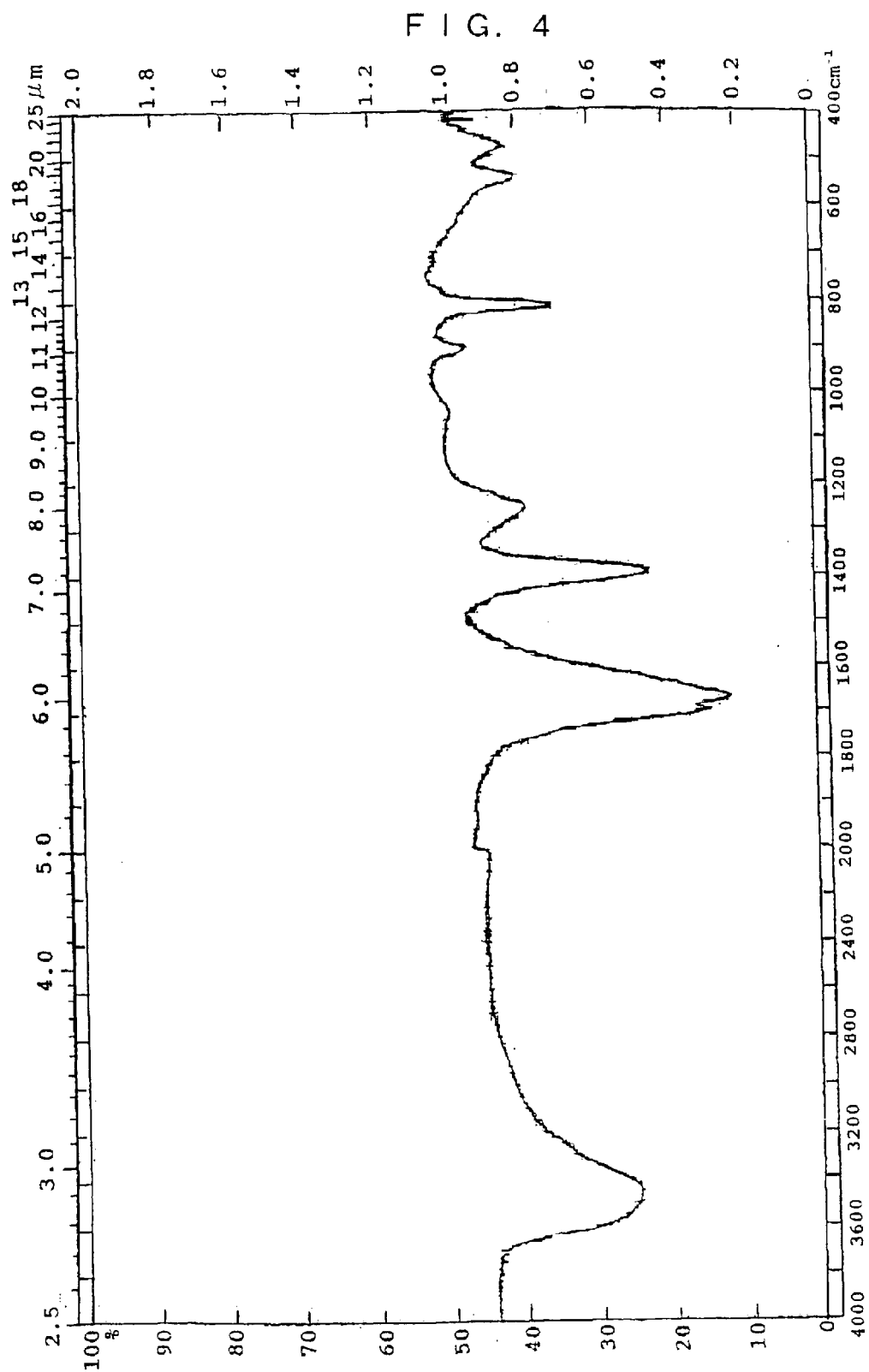
FIG. 4 is an IR spectrum diagram of a complex of ruthenium and oxalic acid obtained in Synthetic Example 10.

The IR spectrum of this product is shown in FIG. 4.

Synthetic Example 11

4.2 g of ruthenium chloride, 2.7 g of sodium formate, 20.0 g of formic acid and 200 ml of ethanol were used to carry out a reaction in the same manner as in Synthetic Example 7 and the reaction product was purified to obtain a complex of ruthenium and an organic carboxylic acid (Ru-formic acid complex). The IR spectrum of the product showed a strong broad absorption derived from COO at 1,560 and 1,625 cm$^{-1}$ and a weak absorption derived from CH at 2,890, 2,940 and 2,960 cm$^{-1}$. The elemental analytical values (wt %) of this product were as follows: Ru 46.94 (47.13), C 11.28 (11.20), H 1.93 (1.88) and O 39.85 (39.79). The figures within the parentheses are calculated values of $Ru_3O(HCOO)_6(H_2O)_3$.

Example 1

Figure 5:
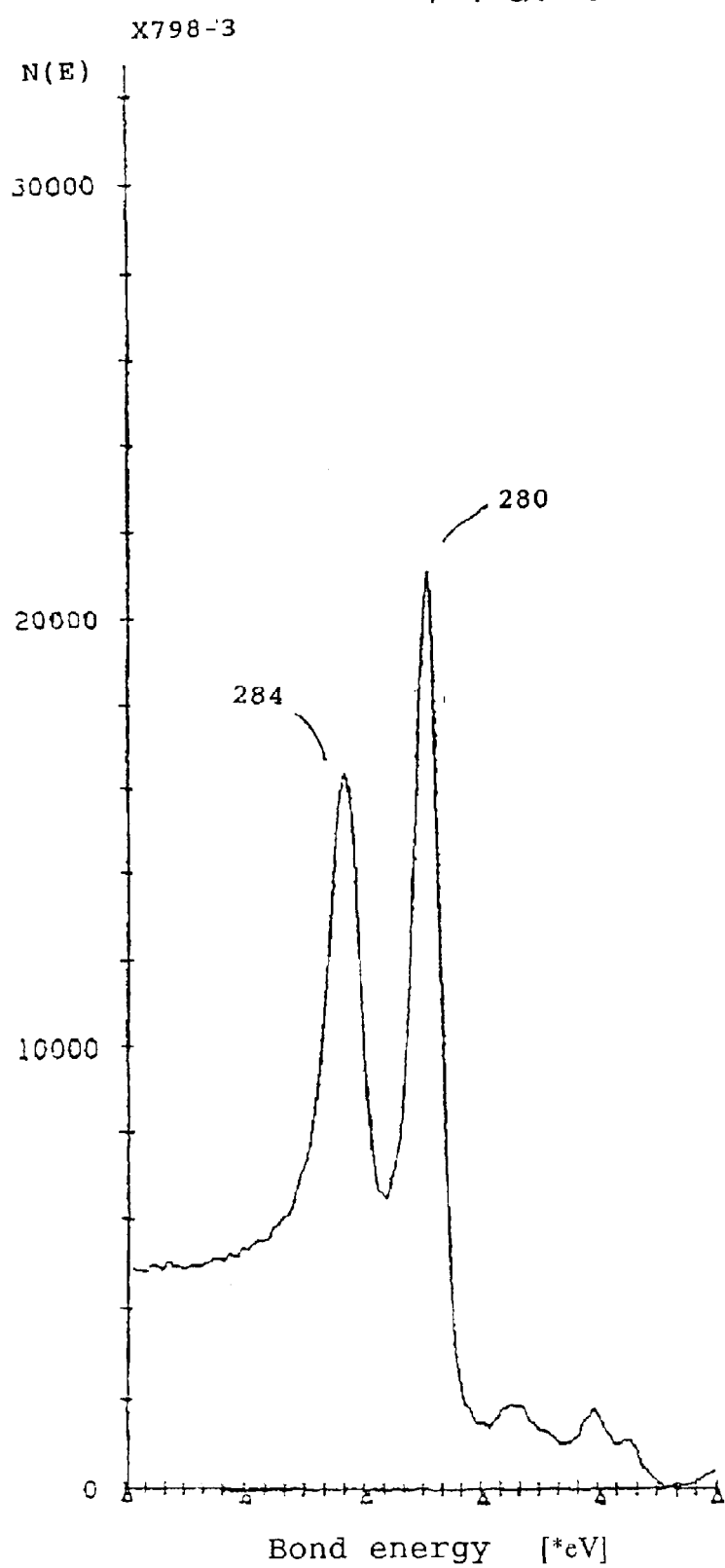
FIG. 5 is an ESCA spectrum diagram of a metal ruthenium film obtained in Example 1.

1 g of the complex of ruthenium and ethyl acetoacetate obtained in the above Synthetic Example 1 was dissolved in 9 g of ethyl lactate to prepare a solution. Foreign matter was removed from this solution by a Teflon filter having an opening diameter of 0.2 μm, and the obtained solution was applied to a quartz substrate in an argon atmosphere by spin coating at 2,000 rpm. After the solvent was evaporated in an argon atmosphere, the coated substrate was heated in an atmosphere of a mixed gas of hydrogen and nitrogen gas (3% of hydrogen) at 500° C. for 30 minutes to form a ruthenium film having a metallic gloss on the substrate. The thickness of this ruthenium film was 700 Å. When the ESCA spectrum of this ruthenium film was measured, a peak derived from the $Ru_{3d}$ orbit was observed at 280 eV and 284 eV and a peak derived from another element was not observed at all. Therefore, it was found that the ruthenium film was a metal ruthenium film. A peak based on carbon was not observed. When the resistivity of this metal ruthenium film was measured by a four-terminal method, it was 45 μΩcm. The ESCA spectrum of the obtained ruthenium film is shown in FIG. 5.

Example 2

Figure 6:
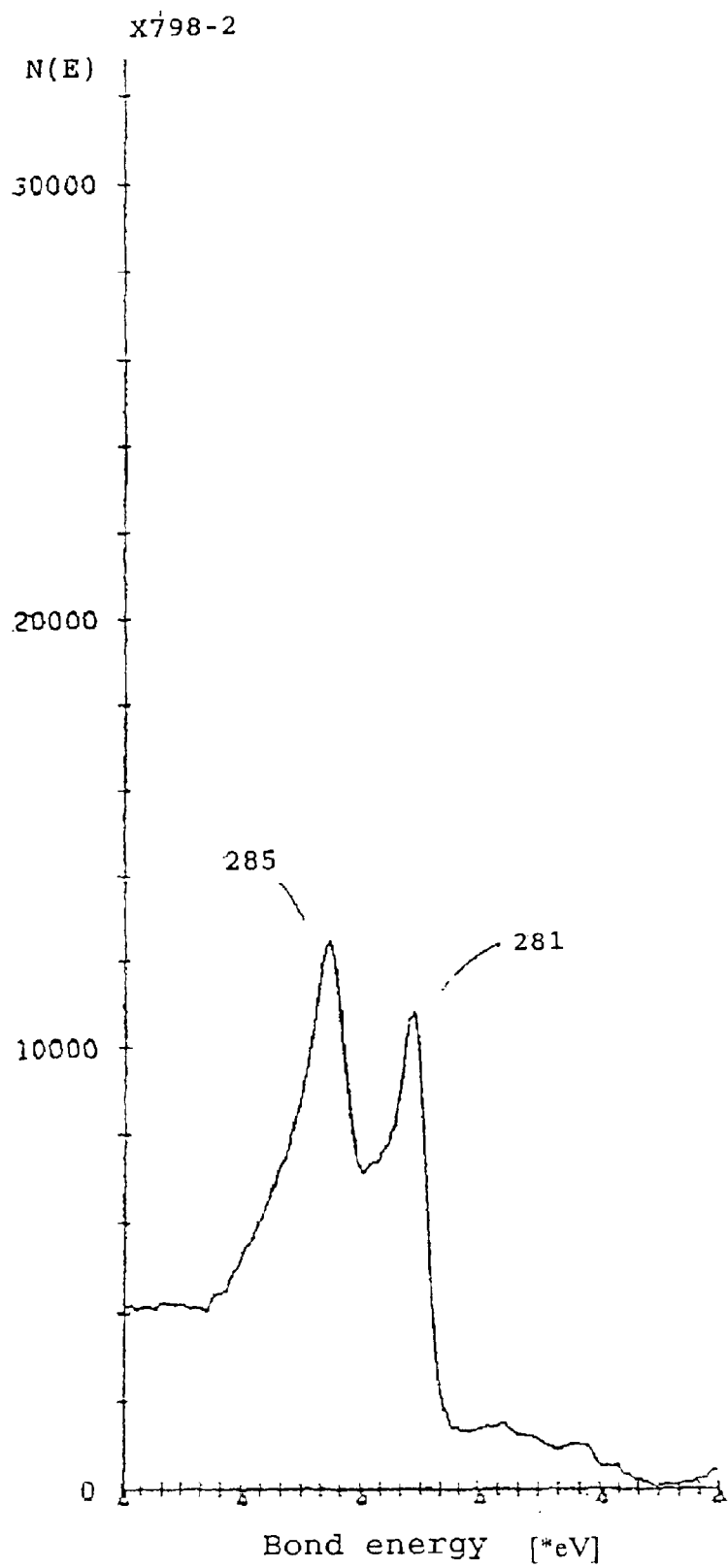
FIG. 6 is an ESCA spectrum diagram of a ruthenium oxide film obtained in Example 2.

1 g of the complex of ruthenium and ethyl acetoacetate obtained in the above Synthetic Example 1 was dissolved in 9 g of ethyl lactate to prepare a coating solution in the same manner as in Example 1. This coating solution was applied to a glass substrate by dip coating. When this coating film was baked at 500° C. in an atmosphere of air for 30 minutes, a slightly blackish film having conductivity was obtained. The thickness of this coating film was 750 Å and the resistivity measured by the four-terminal method thereof was 70 μΩcm. When the ESCA spectrum of the film was measured, a peak derived from the $Ru_{3d}$ orbit was observed at 281 eV and 285 eV and a peak derived from the $O_{1S}$ orbit was observed at the same time, which proved that this coating film was a ruthenium oxide film. A peak based on carbon was not observed from this coating film. The ESCA spectrum of this ruthenium oxide film is shown in FIG. 6.

Example 3

1 g of the ruthenium complex obtained in the above Synthetic Example 2 was dissolved in 4.5 g of ethyl lactate and 4.5 g of ethanol to prepare a solution. Foreign matter was removed from this solution by a Teflon filter having an opening diameter of 0.2 μm, and the obtained solution was applied to a quartz substrate in an argon atmosphere by spin coating at 2,000 rpm. After the solvent was evaporated in an argon atmosphere, the coated substrate was heated at 450° C. in an atmosphere of a mixed gas of hydrogen and nitrogen (3% of hydrogen) for 30 minutes to form a ruthenium film having a metallic gloss on the substrate. The thickness of this ruthenium film was 800 Å. When the ESCA spectrum of this ruthenium film was measured, a peak derived from the $Ru_{3d}$ orbit was observed at 280 eV and 284 eV and a peak derived from another element was not observed at all, which proved that this film was a metal ruthenium film. A peak based on carbon was not observed. When the resistivity of this metal ruthenium film was measured by the four-terminal method, it was 55 μΩcm.

Example 4

1 g of the ruthenium complex obtained in the above Synthetic Example 3 was dissolved in 9 g of ethyl lactate to prepare a solution. Foreign matter was removed from this solution by a Teflon filter having an opening diameter of 0.2 μm, and the obtained solution was applied to a quartz substrate in an argon atmosphere by spin coating at 2,000 rpm. After the solvent was evaporated in an argon atmosphere, the coated substrate was heated at 400° C. in an atmosphere of a mixed gas of hydrogen and nitrogen (3% of hydrogen) for 30 minutes to form a ruthenium film having a metallic gloss on the substrate. The thickness of this ruthenium film was 750 Å. When the ESCA spectrum of this ruthenium film was measured, a peak derived from the $Ru_{3d}$ orbit was observed at 280 eV and 284 eV and a peak derived from another element was not observed at all, which proved that this film was a metal ruthenium film. A peak based on carbon was not observed. When the resistivity of this metal ruthenium film was measured by the four-terminal method, it was 45 μΩcm.

Example 5

1 g of the ruthenium complex obtained in the above Synthetic Example 4 was dissolved in 9 g of ethyl lactate to prepare a solution. Foreign matter was removed from this solution by a Teflon filter having an opening diameter of 0.2 μm, and the obtained solution was applied to a quartz substrate in an argon atmosphere by spin coating at 2,000 rpm. After the solvent was evaporated in an argon atmosphere, the coated substrate was heated at 500° C. in an atmosphere of a mixed gas of hydrogen and nitrogen (3% of hydrogen) for 30 minutes to form a ruthenium film having a metallic gloss on the substrate. The thickness of this ruthenium film was 700 Å. When the ESCA spectrum of this silicon film was measured, a peak derived from the $Ru_{3d}$ orbit was observed at 280 eV and 284 eV and a peak derived from another element was not observed at all, which proved that this film was a metal ruthenium film. A peak based on carbon was not observed. When the resistivity of this metal ruthenium film was measured by the four-terminal method, it was 50 $\mu\Omega$cm.

Example 6

1 g of the ruthenium complex obtained in the above Synthetic Example 5 was dissolved in 9 g of ethyl lactate to prepare a solution. Foreign matter was removed from this solution by a Teflon filter having an opening diameter of 0.2 $\mu$m, and the obtained solution was applied to a quartz substrate in an argon atmosphere by spin coating at 2,000 rpm. After the solvent was evaporated in an argon atmosphere, the coated substrate was heated at 500° C. in an atmosphere of a mixed gas of hydrogen and nitrogen (3% of hydrogen) for 30 minutes to form a ruthenium film having a metallic gloss on the substrate. The thickness of this ruthenium film was 850 Å. When the ESCA spectrum of this silicon film was measured, a peak derived from the $Ru_{3d}$ orbit was observed at 280 eV and 284 eV and a peak derived from another element was not observed at all, which proved that this film was a metal ruthenium film. A peak based on carbon was not observed. When the resistivity of this metal ruthenium film was measured by the four-terminal method, it was 60 $\mu\Omega$cm.

Comparative Example 1

A coating solution was prepared in the same manner as in Example 1 except that $Ru_3(CO)_{12}$ was used in place of the complex of ruthenium and ethyl acetoacetate in Example 1 and chloroform was used as a solvent. When this solution was applied to a glass substrate by spin coating, powdery $Ru_3(CO)_{12}$ remained on the substrate. When this was heated in a nitrogen atmosphere at 400° C., only metal ruthenium having a spotted pattern was obtained.

Example 7

Figure 7:
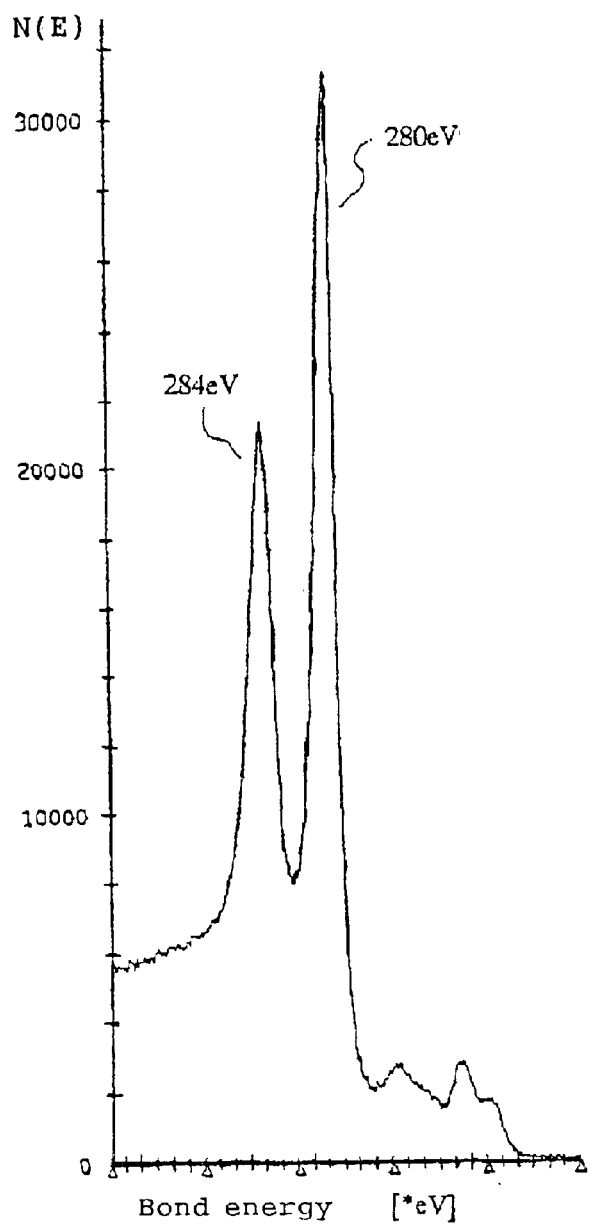
FIG. 7 is an ESCA spectrum diagram of a ruthenium film obtained in Example 7.

1 g of the ruthenium compound Ru(COT)(COD) obtained in the above Synthetic Example 6 was dissolved in 9 g of cyclooctane to prepare a solution. Foreign matter was removed from this solution by a Teflon filter having an opening diameter of 0.2 $\mu$m, and the obtained solution was applied to a quartz substrate in an argon atmosphere by spin coating at 2,000 rpm. After the solvent was evaporated from this coated substrate in an argon atmosphere, the coated substrate was heated at 400° C. in an atmosphere of a mixed gas of hydrogen and nitrogen (3% of hydrogen) for 30 minutes to form a ruthenium film having a metallic gloss on the substrate. The thickness of this ruthenium film was 800 Å. When the ESCA spectrum of this silicon film was measured, a peak derived from the $Ru_{3d}$ orbit was observed at 285.4 eV and 290.6 eV and a peak derived from another element was not observed at all, which proved that this film was a metal ruthenium film. A peak based on carbon was not observed. The ESCA spectrum of this film is shown in FIG. 7. When the resistivity of this metal ruthenium film was measured by the four-terminal method, it was 130 $\mu\Omega$cm.

Example 8

Figure 8:
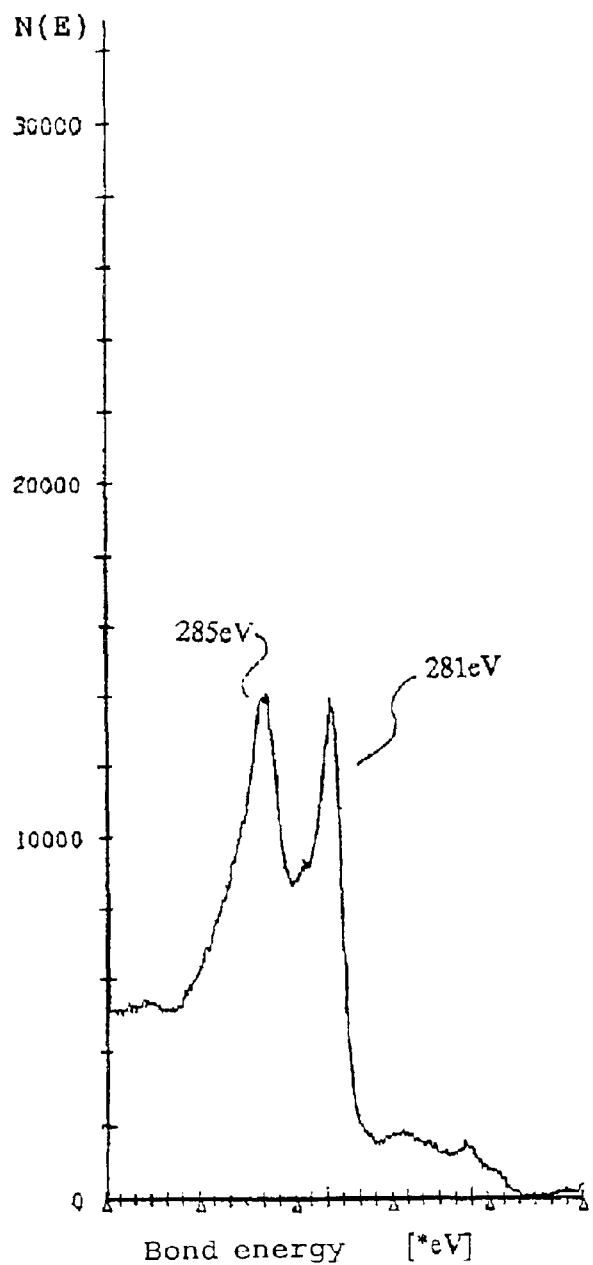
FIG. 8 is an ESCA spectrum diagram of a ruthenium oxide film obtained in Example 8.

1 g of the ruthenium compound Ru(COT)(COD) obtained in the above Synthetic Example 6 was dissolved in 4.5 g of decahydronaphthalene and 4.5 g of n-decane to prepare a coating solution in the same manner as in Example 7. This coating solution was applied to a glass substrate by dip coating. When this coating film was baked at 500° C. in an atmosphere of air for 30 minutes, a slightly blackish coating film having conductivity was obtained. The thickness of this coating film was 650 Å. The resistivity of this film measured by the four-terminal method was 2,400 $\mu\Omega$cm. When the ESCA spectrum of this film was measured, a peak derived from the $Ru_{3d}$ orbit was observed at 285.7 eV and 289.9 eV and a peak derived from the $O_{1S}$ orbit was observed at the same time, which proved that this film was a ruthenium oxide film. A peak based on carbon was not observed. The ESCA spectrum of this film is shown in FIG. 8.

Example 9

Figure 9:
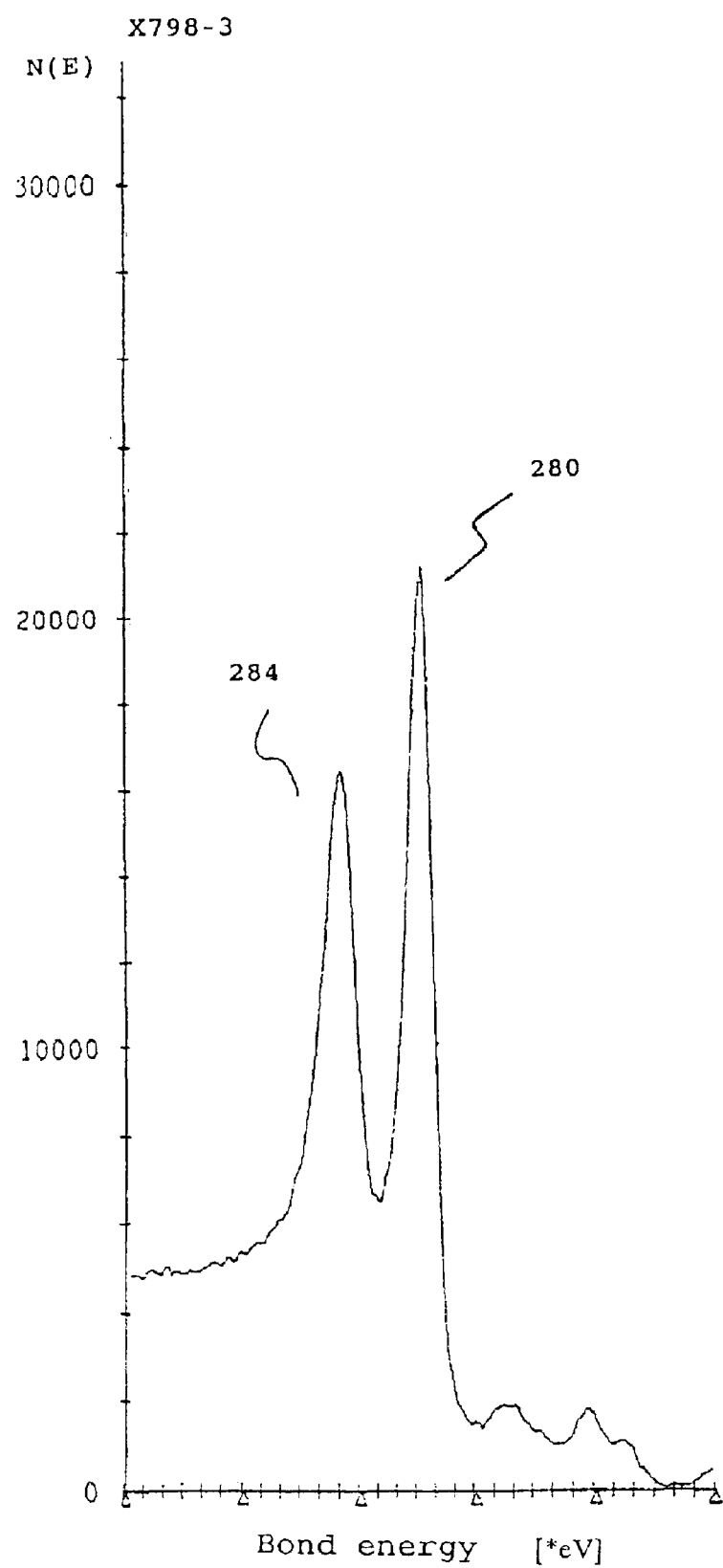
FIG. 9 is an ESCA spectrum diagram of a ruthenium film obtained in Example 9.

1 g of the ruthenium compound obtained in the above Synthetic Example 9 was dissolved in 9 g of cyclohexanol to prepare a solution. Foreign matter was removed from this solution by a Teflon filter having an opening diameter of 0.2 $\mu$m, and the obtained solution was applied to a quartz substrate in an argon atmosphere by spin coating at 2,000 rpm. After the solvent was evaporated in an argon atmosphere, the coated substrate was heated at 450° C. in an atmosphere of a mixed gas of hydrogen and nitrogen (3% of hydrogen) for 30 minutes to form a ruthenium film having a metallic gloss on the substrate. The thickness of this ruthenium film was 800 Å. When the ESCA spectrum of this silicon film was measured, a peak derived from the $Ru_{3d}$ orbit was observed at 280 eV and 284 eV and a peak derived from another element was not observed at all, which proved that this film was a metal ruthenium film. The ESCA spectrum is shown in FIG. 9. A peak based on carbon was not observed. When the resistivity of this metal ruthenium film was measured by the four-terminal method, it was 30 $\mu\Omega$cm.

Example 10

Figure 10:
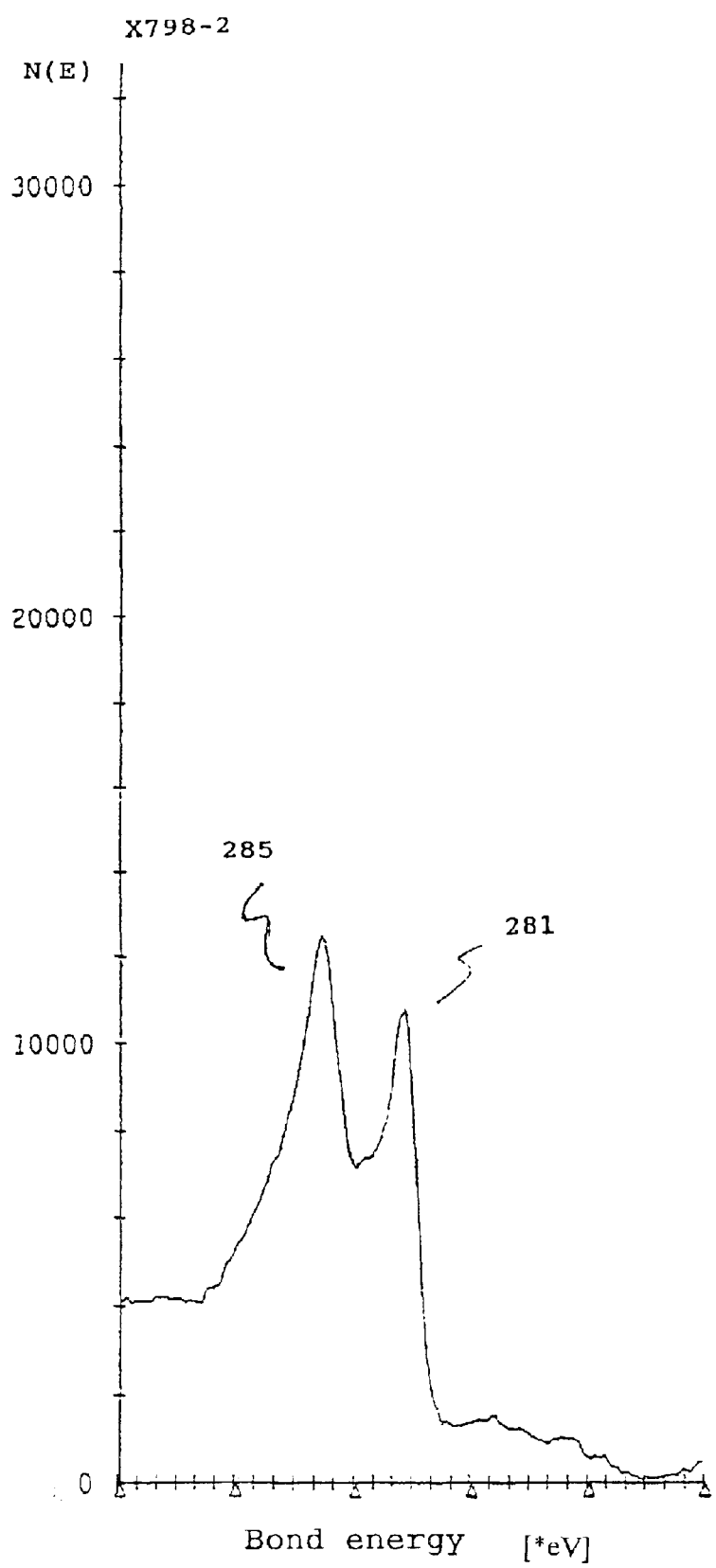
FIG. 10 is an ESCA spectrum diagram of a ruthenium oxide film obtained in Example 10.

A cyclohexane solution of a ruthenium compound was prepared in the same manner as in Example 9 and applied to a quartz substrate. When this substrate was heated at 450° C. in the air for 30 minutes, a slightly blackish film was obtained. The thickness of this film was 700 Å and the resistivity thereof measured by the four-terminal method was 70$\mu\Omega$cm. When the ESCA spectrum of this film was measured, a peak derived from the $Ru_{3d}$ orbit was observed at 281 eV and 285 eV and a peak derived from the $O_{1S}$ orbit was observed at the same time, which proved that this film was a ruthenium oxide film. The ESCA spectrum is shown in FIG. 10.

Example 11

1 g of the ruthenium compound obtained in the above Synthetic Example 7 was dissolved in 9 g of ethanol to prepare a solution. Foreign matter was removed from this solution by a Teflon filter having an opening diameter of 0.2 $\mu$m, and the obtained solution was applied to a quartz substrate in an argon atmosphere by spin coating at 2,000 rpm. After the solvent was evaporated in an argon atmosphere, the coated substrate was heated at 450° C. in an atmosphere of a mixed gas of hydrogen and nitrogen (3% of hydrogen) for 30 minutes to form a ruthenium film having a metallic gloss on the substrate. The thickness of this ruthenium film was 800 Å. When the ESCA spectrum of this ruthenium film was measured, a peak derived from the $Ru_{3d}$ orbit was observed at 280 eV and 284 eV and a peak derived from another element was not observed at all, which proved that this film was a metal ruthenium film. A peak based on carbon was not observed. When the resistivity of this metal ruthenium film was measured by the four-terminal method, it was 25 $\mu\Omega$cm.

Example 12

1 g of the ruthenium compound obtained in the above Synthetic Example 7 was dissolved in a mixed solvent of 4.5 g of ethanol and 4.5 g of toluene to prepare a coating solution in the same manner as in Example 9. This coating solution was applied to a glass substrate by dip coating. After the solvent was evaporated in the air, the coating film was baked at 450° C. in an atmosphere of air for 30 minutes to form a slightly blackish film having conductivity on the substrate. The thickness of this coating film was 650 Å and the resistivity thereof measured by the four-terminal method was 78 $\mu\Omega$cm. When the ESCA spectrum of this film was measured, a peak derived from the $Ru_{3d}$ orbit was observed at 281 eV and 285 eV and a peak derived from the $O_{1S}$ orbit was observed at the same time, which proved that this film was a ruthenium oxide film. A peak based on carbon was not observed.

Example 13

1 g of the ruthenium compound obtained in the above Synthetic Example 8 was dissolved in 9 g of ethanol to prepare a solution. Foreign matter was removed from this solution by a Teflon filter having an opening diameter of 0.2 $\mu$m, and the obtained solution was applied to a quartz substrate in an argon atmosphere by spin coating at 2,000 rpm. After the solvent was evaporated in an argon atmosphere, the coated substrate was heated at 450° C. in an atmosphere of a mixed gas of hydrogen and nitrogen (3% of hydrogen) for 30 minutes to form a ruthenium film having a metallic gloss on the substrate. The thickness of this ruthenium film was 800 Å. When the ESCA spectrum of this silicon film was measured, a peak derived from the $Ru_{3d}$ orbit was observed at 280 eV and 284 eV and a peak derived from another element was not observed at all, which proved that this film was a metal ruthenium film. A peak based on carbon was not observed. When the resistivity of this metal ruthenium film was measured by the four-terminal method, it was 30 $\mu\Omega$cm.

Example 14

Figure 11:
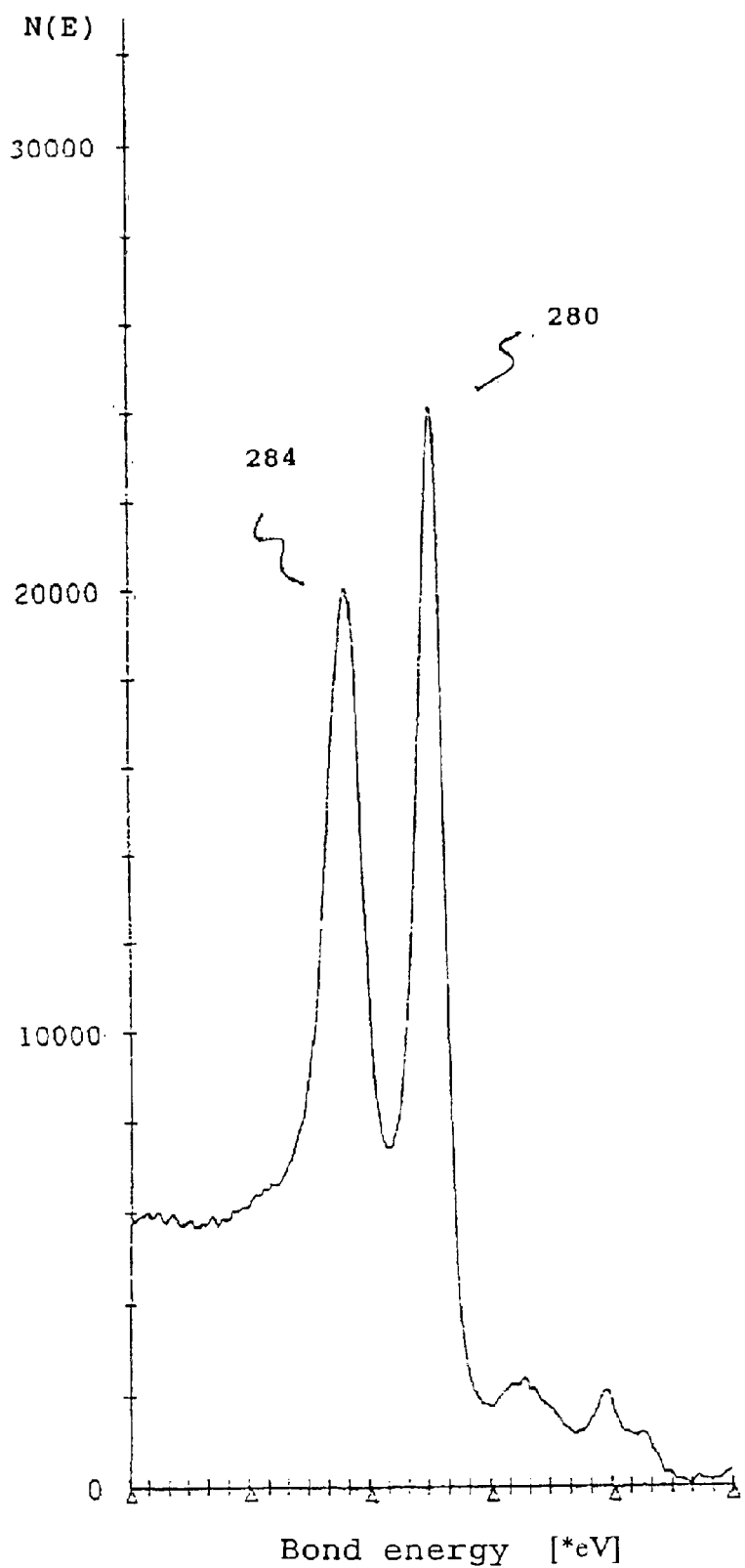
FIG. 11 is an ESCA spectrum diagram of a ruthenium film obtained in Example 14.

1 g of the complex of ruthenium and an organic carboxylic acid obtained in the above Synthetic Example 10 was dissolved in 9 g of ethanol to prepare a solution. Foreign matter was removed from this solution by a Teflon filter having an opening diameter of 0.2 $\mu$m, and the obtained solution was applied to a quartz substrate in an argon atmosphere by spin coating at 2,000 rpm. After the solvent was evaporated in an argon atmosphere, the coated substrate was heated at 450° C. in an atmosphere of a mixed gas of hydrogen and nitrogen (3% of hydrogen) for 30 minutes to form a ruthenium film having a metallic gloss on the substrate. The thickness of this ruthenium film was 800 Å. When the ESCA spectrum of this silicon film was measured, a peak derived from the $Ru_{3d}$ orbit was observed at 280 eV and 284 eV and a peak derived from another element was not observed at all, which proved that this film was a metal ruthenium film. A peak based on carbon was not observed. This ESCA spectrum is shown in FIG. 11. When the resistivity of this metal ruthenium film was measured by the four-terminal method, it was 35 $\mu\Omega$cm.

Example 15

1 g of the ruthenium compound obtained in the above Synthetic Example 11 was dissolved in 9 g of ethanol to prepare a solution. Foreign matter was removed from this solution by a Teflon filter having an opening diameter of 0.2 $\mu$m, and the obtained solution was applied to a quartz substrate in an argon atmosphere by spin coating at 2,000 rpm. After the solvent was evaporated in an argon atmosphere, the coated substrate was heated at 450° C. in an atmosphere of a mixed gas of hydrogen and nitrogen (3% of hydrogen) for 30 minutes to form a ruthenium film having a metallic gloss on the substrate. The thickness of this ruthenium film was 750 Å. When the ESCA spectrum of this silicon film was measured, a peak derived from the $Ru_{3d}$ orbit was observed at 280 eV and 284 eV and a peak derived from another element was not observed at all, which proved that this film was a metal ruthenium film. A peak based on carbon was not observed. When the resistivity of this metal ruthenium film was measured by the four-terminal method, it was 25 $\mu\Omega$cm.

What is claimed is:

1. A solution composition comprising:

at least one ruthenium complex selected from the group consisting of a ruthenium complex represented by the following formula (1):

Ru(COT')(COD')     (1)

wherein COT' is a ligand represented by the following formula (2):

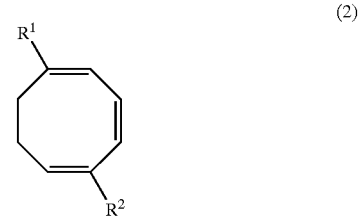

(2)

wherein $R^1$ and $R^2$ are each independently a hydrogen atom or alkyl group having 1 to 5 carbon atoms, and COD' is a ligand represented by the following formula (3):

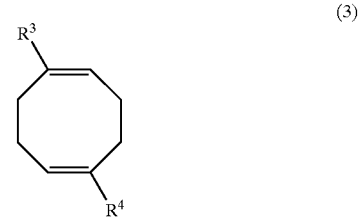

(3)

wherein $R^3$ and $R^4$ are each independently a hydrogen atom or alkyl group having 1 to 5 carbon atoms, and a ruthenium complex having an acyloxy group represented by the following formula (4):

$R^5COO-$     (4)

wherein $R^5$ is a hydrogen atom, alkyl group having 1 to 18 carbon atoms or alkenyl group having 2 to 18 carbon atoms, or a biscarboxylato group represented by the following formula (5):

—OOC—COO— (5), or at least one ruthenium group selected from the group consisting of:

Ru[R$^{15}$—CO—CR$^{16}$—COOR$^{17}$]$_d$[R$^{18}$—CO—CR$^{19}$—COOR$^{20}$]$_e$[R$^{21}$—CO—CR$^{22}$—COOR$^{23}$]$_f$; (7):

Ru[R$^{24}$—OCO—CR$^{25}$—COOR$^{26}$]$_g$[R$^{27}$—OCO—CR$^{28}$—COOR$^{29}$]$_h$[R$^{30}$—OCO—CR$^{31}$—COOR$^{32}$]$_i$; (8):

Ru[R$^6$—CO—CR$^7$—COR$^8$]$_j$[R$^{15}$—CO—CR$^{16}$—COOR$^{17}$]$_k$; (9):

Ru[R$^6$—CO—CR$^7$—COR$^8$]$_l$[R$^{24}$—OCO—CR$^{25}$—COOR$^{26}$]$_m$;(10):

Ru[R$^{15}$—CO—CR$^{16}$—COOR$^{17}$]$_n$[R$^{24}$—OCO—CR$^{25}$—COOR$^{26}$]$_o$; and (11):

Ru[R$^{24}$—OCO—CR$^{25}$—COOR$^{26}$][R$^6$—CO—CR$^7$—COR$^8$][R$^{15}$—CO—CR$^{16}$—COOR$^{17}$]; (12):

wherein d, e, f, g, h and i are each independently an integer of 0 to 3, j, k, l, m, n and o are each independently an integer of 1 or 2, $R^6$, $R^8$, $R^9$, $R^{11}$, $R^{12}$, $R^{14}$, $R^{15}$, $R^{17}$, $R^{18}$, $R^{20}$, $R^{21}$, $R^{23}$, $R^{24}$, $R^{26}$, $R^{27}$, $R^{29}$, $R^{30}$ and $R^{32}$ are each independently an alkyl group having 1 to 18 carbon atoms, alkenyl group having 2 to 18 carbon atoms or aryl group, and the alkyl group or alkenyl group may have a substituent such as a halogen group or alkoxy group, $R^7$, $R^{16}$, $R^{19}$, $R^{22}$, $R^{25}$, $R^{28}$ and $R^{31}$ are each independently an alkyl group having 1 to 18 carbon atoms, alkenyl group having 2 to 18 carbon atoms, alkoxycarbonyl group having an alkyl group with 1 to 18 carbon atoms or alkenyl group, or aryl group having an alkyl group with 1 to 18 carbon atoms or alkenyl group as a substituent, and the alkyl group, the alkyl group in the alkenyl group and alkoxy group, or the alkenyl group may have a substituent such as a halogen group or alkoxy group, and with the proviso that d+e+f=3, g+h+i=3, j+k=3, l+m=3, and n+o=3.

2. A film comprising at least one ruthenium complex selected from the group consisting of a ruthenium complex represented by the following formula (1):

Ru(COT')(COD') (1)

wherein COT' is a ligand represented by the following formula (2):

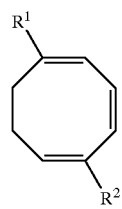

(2)

wherein $R^1$ and $R^2$ are each independently a hydrogen atom or alkyl group having 1 to 5 carbon atoms, and COD' is a ligand represented by the following formula (3):

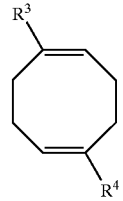

(3)

wherein $R^3$ and $R^4$ are each independently a hydrogen atom or alkyl group having 1 to 5 carbon atoms, and a ruthenium complex having an acyloxy group represented by the following formula (4):

R$^5$COO— (4)

wherein $R^5$ is a hydrogen atom, alkyl group having 1 to 18 carbon atoms or alkenyl group having 2 to 18 carbon atoms, or a biscarboxylato group represented by the following formula (5):

—OOC—COO— (5), or at least one ruthenium group selected from the group consisting of:

Ru[R$^{15}$—CO—CR$^{16}$—COOR$^{17}$]$_d$[R$^{18}$—CO—CR$^{19}$—COOR$^{20}$]$_e$[R$^{21}$—CO—CR$^{22}$—COOR$^{23}$]$_f$; (7):

Ru[R$^{24}$—OCO—CR$^{25}$—COOR$^{26}$]$_g$[R$^{27}$—OCO—CR$^{28}$—COOR$^{29}$]$_h$[R$^{30}$—OCO—CR$^{31}$—COOR$^{32}$]$_i$; (8):

Ru[R$^6$—CO—CR$^7$—COR$^8$]$_j$[R$^{15}$—CO—CR$^{16}$—COOR$^{17}$]$_k$; (9):

Ru[R$^6$—CO—CR$^7$—COR$^8$]$_l$[R$^{24}$—OCO—CR$^{25}$—COOR$^{26}$]$_m$;(10):

Ru[R$^{15}$—CO—CR$^{16}$—COOR$^{17}$]$_n$[R$^{24}$—OCO—CR$^{25}$—COOR$^{26}$]$_o$; and (11):

Ru[R$^{24}$—OCO—CR$^{25}$—COOR$^{26}$][R$^6$—CO—CR$^7$—COR$^8$][R$^{15}$—CO—CR$^{16}$—COOR$^{17}$]; (12):

wherein d, e, f, g, h and i are each independently an integer of 0 to 3, j, k, l, m, n and o are each independently an integer of 1 or 2, $R^6$, $R^8$, $R^9$, $R^{11}$, $R^{12}$, $R^{14}$, $R^{15}$, $R^{17}$, $R^{18}$, $R^{20}$, $R^{21}$, $R^{23}$, $R^{24}$, $R^{26}$, $R^{27}$, $R^{29}$, $R^{30}$ and $R^{32}$ are each independently an alkyl group having 1 to 18 carbon atoms, alkenyl group having 2 to 18 carbon atoms or aryl group, and the alkyl group or alkenyl group may have a substituent such as a halogen group or alkoxy group, $R^7$, $R^{16}$, $R^{19}$, $R^{22}$, $R^{25}$, $R^{28}$ and $R^{31}$ are each independently an alkyl group having 1 to 18 carbon atoms, alkenyl group having 2 to 18 carbon atoms, alkoxycarbonyl group having an alkyl group with 1 to 18 carbon atoms or alkenyl group, or aryl group having an alkyl group with 1 to 18 carbon atoms or alkenyl group as a substituent, and the alkyl group, the alkyl group in the alkenyl group and alkoxy group, or the alkenyl group may have a substituent such as a halogen group or alkoxy group, and with the proviso that d+e+f=3, g+h+i=3, j+k=3, l+m=3, and n+o=3.

3. A process for forming a ruthenium film, comprising
applying the solution composition of claim 1 to a substrate and heating it in an atmosphere containing substantially no oxygen.

4. A process for forming a ruthenium oxide film, comprising
applying the solution composition of claim 1 to a substrate and heating it in an atmosphere containing oxygen.

5. A ruthenium film formed by the process of claim 3.

6. A ruthenium oxide film formed by the process of claim 4.

7. A process for forming a ruthenium electrode, comprising applying the solution composition of claim 1 to a substrate and heating it in an atmosphere containing substantially no oxygen.

8. A process for forming a ruthenium oxide electrode, comprising
applying the solution composition of claim 1 to a substrate and heating it in an atmosphere containing oxygen.

9. An electrode formed by the process of claim 7.

10. An electrode formed by the process of claim 8.

11. The solution composition of claim 1 comprising a ruthenium complex represented by the following formula (1):

$$Ru(COT')(COD') \qquad (1)$$

wherein COT' is a ligand represented by the following formula (2):

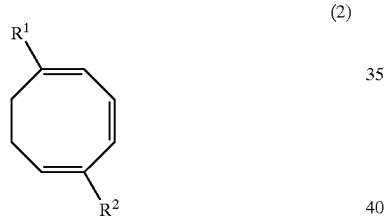

(2)

wherein $R^1$ and $R^2$ are each independently a hydrogen atom or alkyl group having 1 to 5 carbon atoms, and COD' is a ligand represented by the following formula (3):

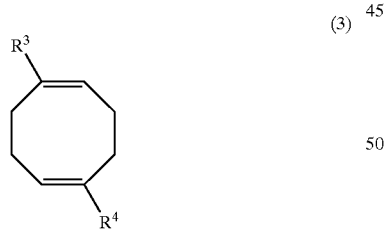

(3)

wherein $R^3$ and $R^4$ are each independently a hydrogen atom or alkyl group having 1 to 5 carbon atoms.

12. The solution composition of claim 1 comprising:
a ruthenium complex having an acyloxy group represented by the following formula (4):

$$R^5COO— \qquad (4)$$

wherein $R^5$ is a hydrogen atom, alkyl group having 1 to 18 carbon atoms or alkenyl group having 2 to 18 carbon atoms, or a biscarboxylato group represented by the following formula (5):

$$—OOC—COO— \qquad (5).$$

13. The solution composition of claim 1 comprising:
a ruthenium complex selected from the group consisting of:

$$Ru[R^{15}—CO—CR^{16}—COOR^{17}]_d[R^{18}—CO—CR^{19}—COOR^{20}]_e[R^{21}—CO—CR^{22}—COOR^{23}]_f; \qquad (7):$$

$$Ru[R^{24}—OCO—CR^{25}—COOR^{26}]_g[R^{27}—OCO—CR^{28}—COOR^{29}]_h[R^{30}—OCO—CR^{31}—COOR^{32}]_i; \qquad (8):$$

$$Ru[R^6—CO—CR^7—COR^8]_j[R^{15}—CO—CR^{16}—COOR^{17}]_k; \qquad (9):$$

$$Ru[R^6—CO—CR^7—COR^8]_l[R^{24}—OCO—CR^{25}—COOR^{26}]_m; (10):$$

$$Ru[R^{15}—CO—CR^{16}—COOR^{17}]_n[R^{24}—OCO—CR^{25}—COOR^{26}]_o; \text{ and} \qquad (11):$$

$$Ru[R^{24}—OCO—CR^{25}—COOR^{26}][R^6—CO—CR^7—COR^8][R^{15}—CO—CR^{16}—COOR^{17}]; \qquad (12):$$

wherein d, e, f, g, h and i are each independently an integer of 0 to 3, j, k, l, m, n and o are each independently an integer of 1 or 2, $R^6, R^8, R^9, R^{11}, R^{12}, R^{14}, R^{15}, R^{17}, R^{18}, R^{20}, R^{21}, R^{23}, R^{24}, R^{26}, R^{27}, R^{29}, R^{30}$ and $R^{32}$ are each independently an alkyl group having 1 to 18 carbon atoms, alkenyl group having 2 to 18 carbon atoms or aryl group, and the alkyl group or alkenyl group may have a substituent such as a halogen group or alkoxy group, $R^7, R^{16}, R^{19}, R^{22}, R^{25}, R^{28}$ and $R^{31}$ are each independently an alkyl group having 1 to 18 carbon atoms, alkenyl group having 2 to 18 carbon atoms, alkoxycarbonyl group having an alkyl group with 1 to 18 carbon atoms or alkenyl group, or aryl group having an alkyl group with 1 to 18 carbon atoms or alkenyl group as a substituent, and the alkyl group, the alkyl group in the alkenyl group and alkoxy group, or the alkenyl group may have a substituent such as a halogen group or alkoxy group, with the proviso that d+e+f=3, g+h+i=3, j+k=3, l+m=3, and n+o=3.

14. The film of claim 2 comprising a ruthenium complex represented by the following formula (1):

$$Ru(COT')(COD') \qquad (1)$$

wherein COT' is a ligand represented by the following formula (2):

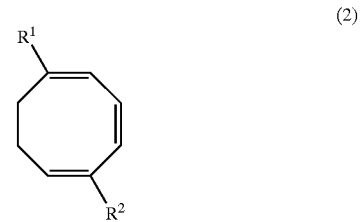

(2)

wherein $R^1$ and $R^2$ are each independently a hydrogen atom or alkyl group having 1 to 5 carbon atoms, and COD' is a ligand represented by the following formula (3):

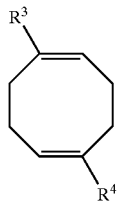  (3)

wherein $R^3$ and $R^4$ are each independently a hydrogen atom or alkyl group having 1 to 5 carbon atoms.

15. The film of claim 2 comprising:

a ruthenium complex having an acyloxy group represented by the following formula (4):

$$R^5COO— \qquad (4)$$

wherein $R^5$ is a hydrogen atom, alkyl group having 1 to 18 carbon atoms or alkenyl group having 2 to 18 carbon atoms, or a biscarboxylato group represented by the following formula (5):

$$—OOC—COO— \qquad (5).$$

16. The film of claim 2 comprising:

a ruthenium complex selected from the group consisting of:

$Ru[R^{15}—CO—CR^{16}—COOR^{17}]_d[R^{18}—CO—CR^{19}—COOR^{20}]_e[R^{21}—CO—CR^{22}—COOR^{23}]_f;$  (7)

$Ru[R^{24}—OCO—CR^{25}—COOR^{26}]_g[R^{27}—OCO—CR^{28}—COOR^{29}]_h[R^{30}—OCO—CR^{31}—COOR^{32}]_i;$  (8)

$Ru[R^6—CO—CR^7—COR^8]_j[R^{15}—CO—CR^{16}—COOR^{17}]_k;$  (9)

$Ru[R^6—CO—CR^7—COR^8]_l[R^{24}—OCO—CR^{25}—COOR^{26}]_m;$ (10)

$Ru[R^{15}—CO—CR^{16}—COOR^{17}]_n[R^{24}—OCO—CR^{25}—COOR^{26}]_o;$ and  (11)

$Ru[R^{24}—OCO—CR^{25}—COOR^{26}][R^6—CO—CR^7—COR^8][R^{15}—CO—CR^{16}—COOR^{17}];$  (12)

wherein d, e, f, g, h and i are each independently an integer of 0 to 3, j, k, l, m, n and o are each independently an integer of 1 or 2, $R^6$, $R^8$, $R^9$, $R^{11}$, $R^{12}$, $R^{14}$, $R^{15}$, $R^{17}$, $R^{18}$, $R^{20}$, $R^{21}$, $R^{23}$, $R^{24}$, $R^{26}$, $R^{27}$, $R^{29}$, $R^{30}$ and $R^{32}$ are each independently an alkyl group having 1 to 18 carbon atoms, alkenyl group having 2 to 18 carbon atoms or aryl group, and the alkyl group or alkenyl group may have a substituent such as a halogen group or alkoxy group, $R^7$, $R^{16}$, $R^{19}$, $R^{22}$, $R^{25}$, $R^{28}$ and $R^{31}$ are each independently an alkyl group having 1 to 18 carbon atoms, alkenyl group having 2 to 18 carbon atoms, alkoxycarbonyl group having an alkyl group with 1 to 18 carbon atoms or alkenyl group, or aryl group having an alkyl group with 1 to 18 carbon atoms or alkenyl group as a substituent, and the alkyl group, the alkyl group in the alkenyl group and alkoxy group, or the alkenyl group may have a substituent such as a halogen group or alkoxy group, with the proviso that d+e+f=3, g+h+i=3, j+k=3, l+m=3, and n+o=3.

* * * * *